US011905542B2

(12) United States Patent
Balch et al.

(10) Patent No.: US 11,905,542 B2
(45) Date of Patent: Feb. 20, 2024

(54) PRODUCTION OF RETINYL ESTERS

(71) Applicant: DSM IP ASSETS B.V., Heerlen (NL)

(72) Inventors: Nathalie Balch, Kaiseraugst (CH); Paul Blomquist, Kaiseraugst (CH); Reed Doten, Kaiseraugst (CH); Peter Houston, Kaiseraugst (CH); Ethan Lam, Kaiseraugst (CH); Jenna McMahon, Kaiseraugst (CH); Joshua Trueheart, Kaiseraugst (CH); Celine Viarouge, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 49 days.

(21) Appl. No.: 16/648,872

(22) PCT Filed: Sep. 25, 2018

(86) PCT No.: PCT/EP2018/076021
§ 371 (c)(1),
(2) Date: Mar. 19, 2020

(87) PCT Pub. No.: WO2019/057996
PCT Pub. Date: Mar. 28, 2019

(65) Prior Publication Data
US 2020/0239924 A1    Jul. 30, 2020

Related U.S. Application Data

(60) Provisional application No. 62/562,680, filed on Sep. 25, 2017.

(51) Int. Cl.
C12P 23/00    (2006.01)

(52) U.S. Cl.
CPC ................................. C12P 23/00 (2013.01)

(58) Field of Classification Search
CPC ........................................................ C12P 23/00
See application file for complete search history.

(56) References Cited

U.S. PATENT DOCUMENTS

| 2004/0038209 A1 | 2/2004 | Lintig et al. |
| 2011/0039299 A1 | 2/2011 | Bailey et al. |

FOREIGN PATENT DOCUMENTS

| CN | 101218352 A | 7/2008 | |
| JP | 2003-518382 | 6/2003 | |
| WO | 2006/102342 | 9/2006 | |
| WO | WO-2006102342 A2 * | 9/2006 | ............. A23L 31/00 |

OTHER PUBLICATIONS

Hong, S. H., Kim, K. R., & Oh, D. K. (2015). Biochemical properties of retinoid-converting enzymes and biotechnological production of retinoids. Applied microbiology and biotechnology, 99(19), 7813-7826. (Year: 2015).*
Expasy enzyme classifications (Year: 2022).*
Seung-Hye Hong, et al., "Biochemical properties of retinoid-converting enzymes and biotechnological production of retinoids", Applied Microbiology and Biotechnology, vol. 99, No. 19, Aug. 1, 2015, pp. 7813-7826.
Hui-Jeong Jang, et al., "Retinoid production using metabolically engineered *Echerichia coli* with a two-phase culture system", Microbial Cell Factories, vol. 10, No. 1, Jul. 29, 2011, 12 pages.
Sheila M. O'Byrne, et al., "Retinol and retinyl esters: biochemistry and physiology: Thematic Review Series: Fat-Soluble Vitamins: Vitamin A", Journal of Lipid Research, vol. 54, No. 7, Jul. 1, 2013, pp. 1731-1743.
International Search Report for PCT/EP2018/076021 dated Dec. 6, 2018, 5 pages.
Written Opinion of the ISA for PCT/EP2018/076021 dated Dec. 6, 2018, 7 pages.
Alberto Ruiz et al., "Molecular and Biochemical Characterization of Lecithin Retinol Acyltransferase" The Journal of Biological Chemistry, vol. 274, No. 6, 1999, pp. 3834-3841.
Renate Schreiber et al., "Retinyl ester hydrolases and their roles in vitamin A homeostasis", Biochim Biophys Acta. 2012, pp. 113-123.
Chi-Liang Eric Yen et al. "DGAT enzymes and triacylglycerol biosynthesis", Journal of Lipid Research, vol. 49, 2008, pp. 2283-2301.

* cited by examiner

*Primary Examiner* — Robert J Yamasaki
*Assistant Examiner* — Trevor Kane
(74) *Attorney, Agent, or Firm* — Nixon & Vanderhye, PC

(57) ABSTRACT

The present invention is related to a novel enzymatic process for production of retinyl esters, such as in particular retinyl long chain esters, via conversion of retinol, which process includes the use of enzymes having acyltransferase activity. Said process might be used for biotechnological production of vitamin A.

13 Claims, No Drawings
Specification includes a Sequence Listing.

SEQUENCE LISTING

<160> NUMBER OF SEQ ID NOS: 17

<210> SEQ ID NO 1
<211> LENGTH: 1698
<212> TYPE: DNA
<213> ORGANISM: Artificial Sequence
<220> FEATURE:
<223> OTHER INFORMATION: Yarrowia codon optimized DmDGA1

<400> SEQUENCE: 1

```
atgaccacta acaaggaccc tcaggataag gagcccggta aggccgagca gcccactaag      60
aactctggtt cctccggtgt gggcattatg aagcgacttc gacgatctgc ctccgccact     120
gagcacaacc tttcttccct gcgaaaccga aagtccactc agaaccttt cgatcagcac      180 ggcaaccta ttgaccttcg acagtaccga aaggttcttg acaaggatga gaacggtaac      240
ggaaccaacg gctctgagaa gaagctccga taccgacgaa ctcagtctgt tacccgagct     300
gaggagattt ctaacaagga ggagaagcag cgacgagccc agcctggccg acctattcac     360
cgaccccgag attctctttt ctcttggtcc tctggattca ctaactttc tggtctggtc      420 aactggggat tccttctcct ctgtatcgga ggtctgcgac ttggccttga gaaccttctc     480
aagtacggta tccgaatcaa ccctctcgat tggttcttct tcatttccgg acacaacgag     540
ggtgagggac acaacgctct gatcctgtcc atttactctc ttgttcacat ctccctctgt     600
cttgctgtcg agaagggtct ggctatggag attattgctg agggccttgg tctgttcatc     660
cagattgtga acattgttgt tctcgtttgt ctgcccgtgg ttactattca ccttaaggga     720
cacgcttttt ctcttatggg agcctctact gtttgcttct tttactctgt tctcttcctt     780
aagctctggt cttacgtgca gactaacatg tggtgccgac agacttacta ccagaagaac     840
ccccgagagc gacgaccttc cattactctc gccgagctta agaagggagt tcttaacgga     900
ggtgaggagg atgaggacgt ttccaagctg gttcagtacc ctgacaacct tacctacaag     960
gatctcctgt acttcctttg cgcccccact ctctgttacg agcttaactt ccctcgaact    1020
tcccgagtgc gaaagcgatt tctccttaag cgactccttg aggtggtcat tggtgtgaac    1080
gttgttatgg ccctttcca gcagtggatt atcccttctg tgcgaaactc ccttatcccc    1140
ttctctaaca tggacgtggc ccttgctact gagcgacttc tcaagctggc tctccctaac    1200 caccttgct ggctctgctt tttctacctt atgttccact cttttctcaa cgctgtcggc     1260
gagcttctca actttgctga tcgaaacttt tactgtgatt ggtggaacgc taacaacatt    1320
gacaccttct ggcgaacttg gaacatgcct gttcaccgat ggtgcgtgcg acacctttac    1380
```

| attcccgtgg ttcagatggg atactcttct cgacaggctt ccactattgt ctttctcttt | 1440 |
| tctgccgtct ttcacgagta ccttgtttct gttcccttc agatttacaa gatttgggct | 1500 |
| tttatgggca tgatgggtca gattcccctt ccgccatttt ccaagtctat tgagaagaag | 1560 |
| ctcggccctc gaatgggaaa cattatcgtg tgggcttcca ttattcttgg tcagcctctc | 1620 |
| tgtatcatgg cttactacca cgattacgtc gttcagcact ttaagaactc cctcaacggc | 1680 |
| accgactact cttcctaa | 1698 |

```
<210> SEQ ID NO 2
<211> LENGTH: 1467
<212> TYPE: DNA
<213> ORGANISM: Artificial Sequence
<220> FEATURE:
<223> OTHER INFORMATION: Yarrowia codon optimized YlDGA1

<400> SEQUENCE: 2
```

| atgggtgatc gaggctcctc ccgacgacga cgaactggct cccgacccctc ctcccacggc | 60 |
| ggcggcggcc ctgccgccgc tgaggaggag gtgcgagatg ccgctgccgg ccccgacgtg | 120 |
| ggcgctgccg cgacgccccc tgccccgcc cccaacaagg atggcgacgc tggcgtgggc | 180 |
| tccgccact gggagctgcg atgccaccga ctccaggatt ctcttttctc ttccgactct | 240 |
| ggcttctcca actaccgagg catcctgaac tggtgtgtcg tgatgctgat cctttctaac | 300 |
| gcccgacttt tccttgagaa cctcatcaag tacggtatcc tggtcgatcc catccaggtc | 360 |
| gtttctctgt tcctgaagga cccttactcc tggcccgccc cttgcctggt tattgccgcc | 420 |
| aacgttttttg ccgttgctgc tttccaggtt gagaagcgac tggccgtggg tgccctgacc | 480 |
| gagcaggccg gactcctgct ccacgtggcc aacctcgcca ccattctgtg tttccctgcc | 540 |
| gctgtggttc ttctcgttga gtctattacc cctgtcggct ccctcctggc tctgatggcc | 600 |
| cacaccatcc tcttcctcaa gctgttctcc taccgagatg tcaactcttg gtgccgacga | 660 |
| gcccgagcca aggctgcctc tgctggcaag aaggcttcct ctgctgctgc cccccacact | 720 |
| gtctcctacc ccgacaacct tacctaccga gatctctact acttcctctt cgcccccact | 780 |
| ctctgctacg agctcaactt tccccgatcc cccgaatcc gaaagcgatt cctccttcga | 840 |
| cgaatccttg agatgctctt tttcacccag ctccaggtgg gcctgatcca gcagtggatg | 900 |
| gtccccacca tccagaactc catgaagccc tttaaggaca tggactactc ccgaatcatc | 960 |
| gagcgactcc tgaagctggc cgtccctaac cacctcatct ggctcatctt cttctactgg | 1020 |
| ctgttccact cctgcctgaa cgctgtggcc gagctcatgc agtttggcga ccagagagttc | 1080 |
| taccgagact ggtggaactc cgagtctgtc acctacttct ggcagaactg gaacattccc | 1140 |
| gtgcacaagt ggtgcattcg acacttctac aagcccatgc ttcgacgagg ctcctctaag | 1200 |
| tggatggccc gaactggcgt gttcctggcc tccgccttct ccacgagta cctcgtgtcc | 1260 |
| gtccctctcc gaatgttccg actctgggcc ttcaccggca tgatggctca gatccctctc | 1320 |
| gcctggttcg tgggtcgatt cttccagggc aactacggta acgctgctgt gtggctgtcc | 1380 |
| ctcatcatcg acagcctat tgccgtcctc atgtacgtcc acgactacta cgtgctcaac | 1440 |
| tacgaggctc ccgctgccga ggcttag | 1467 |

```
<210> SEQ ID NO 3
<211> LENGTH: 565
<212> TYPE: PRT
<213> ORGANISM: Drosophila melanogaster

<400> SEQUENCE: 3
```

```
Met Thr Thr Asn Lys Asp Pro Gln Asp Lys Glu Pro Gly Lys Ala Glu
1               5                   10                  15

Gln Pro Thr Lys Asn Ser Gly Ser Ser Gly Val Gly Ile Met Lys Arg
            20                  25                  30

Leu Arg Arg Ser Ala Ser Ala Thr Glu His Asn Leu Ser Ser Leu Arg
        35                  40                  45

Asn Arg Lys Ser Thr Gln Asn Leu Phe Asp Gln His Gly Asn Pro Ile
    50                  55                  60

Asp Leu Arg Gln Tyr Arg Lys Val Leu Asp Lys Asp Glu Asn Gly Asn
65                  70                  75                  80

Gly Thr Asn Gly Ser Glu Lys Lys Leu Arg Tyr Arg Arg Thr Gln Ser
                85                  90                  95

Val Thr Arg Ala Glu Glu Ile Ser Asn Lys Glu Glu Lys Gln Arg Arg
                100                 105                 110

Ala Gln Pro Gly Arg Pro Ile His Arg Pro Arg Asp Ser Leu Phe Ser
            115                 120                 125

Trp Ser Ser Gly Phe Thr Asn Phe Ser Gly Leu Val Asn Trp Gly Phe
    130                 135                 140

Leu Leu Leu Cys Ile Gly Gly Leu Arg Leu Gly Leu Glu Asn Leu Leu
145                 150                 155                 160

Lys Tyr Gly Ile Arg Ile Asn Pro Leu Asp Trp Phe Phe Ile Ser
                165                 170                 175

Gly His Asn Glu Gly Glu Gly His Asn Ala Leu Ile Leu Ser Ile Tyr
                180                 185                 190

Ser Leu Val His Ile Ser Leu Cys Leu Ala Val Glu Lys Gly Leu Ala
            195                 200                 205

Met Glu Ile Ile Ala Glu Gly Leu Gly Leu Phe Ile Gln Ile Val Asn
    210                 215                 220

Ile Val Val Leu Val Cys Leu Pro Val Val Thr Ile His Leu Lys Gly
225                 230                 235                 240

His Ala Phe Ser Leu Met Gly Ala Ser Thr Val Cys Phe Phe Tyr Ser
            245                 250                 255

Val Leu Phe Leu Lys Leu Trp Ser Tyr Val Gln Thr Asn Met Trp Cys
            260                 265                 270

Arg Gln Thr Tyr Tyr Gln Lys Asn Pro Arg Glu Arg Arg Pro Ser Ile
    275                 280                 285

Thr Leu Ala Glu Leu Lys Lys Gly Val Leu Asn Gly Gly Glu Glu Asp
    290                 295                 300

Glu Asp Val Ser Lys Leu Val Gln Tyr Pro Asp Asn Leu Thr Tyr Lys
305                 310                 315                 320

Asp Leu Leu Tyr Phe Leu Cys Ala Pro Thr Leu Cys Tyr Glu Leu Asn
            325                 330                 335

Phe Pro Arg Thr Ser Arg Val Arg Lys Arg Phe Leu Leu Lys Arg Leu
            340                 345                 350

Leu Glu Val Val Ile Gly Val Asn Val Met Ala Leu Phe Gln Gln
    355                 360                 365

Trp Ile Ile Pro Ser Val Arg Asn Ser Leu Ile Pro Phe Ser Asn Met
    370                 375                 380

Asp Val Ala Leu Ala Thr Glu Arg Leu Leu Lys Leu Ala Leu Pro Asn
385                 390                 395                 400

His Leu Cys Trp Leu Cys Phe Phe Tyr Leu Met Phe His Ser Phe Leu
            405                 410                 415
```

```
Asn Ala Val Gly Glu Leu Leu Asn Phe Ala Asp Arg Asn Phe Tyr Cys
                420                 425                 430
Asp Trp Trp Asn Ala Asn Asn Ile Asp Thr Phe Trp Arg Thr Trp Asn
            435                 440                 445
Met Pro Val His Arg Trp Cys Val Arg His Leu Tyr Ile Pro Val Val
        450                 455                 460
Gln Met Gly Tyr Ser Ser Arg Gln Ala Ser Thr Ile Val Phe Leu Phe
465                 470                 475                 480
Ser Ala Val Phe His Glu Tyr Leu Val Ser Val Pro Leu Gln Ile Tyr
                485                 490                 495
Lys Ile Trp Ala Phe Met Gly Met Met Gly Gln Ile Pro Leu Ser Ala
            500                 505                 510
Ile Ser Lys Ser Ile Glu Lys Lys Leu Gly Pro Arg Met Gly Asn Ile
        515                 520                 525
Ile Val Trp Ala Ser Ile Ile Leu Gly Gln Pro Leu Cys Ile Met Ala
        530                 535                 540
Tyr Tyr His Asp Tyr Val Val Gln His Phe Lys Asn Ser Leu Asn Gly
545                 550                 555                 560
Thr Asp Tyr Ser Ser
                565

<210> SEQ ID NO 4
<211> LENGTH: 2090
<212> TYPE: DNA
<213> ORGANISM: Drosophila melanogaster

<400> SEQUENCE: 4
gcgtcagttg agaactcgtc gttgaagcgt gcggtttacg gtaaaaagag gccgcttcca      60
gtacgtgaaa ataagtctgc tcttgttgaa agaaacaaca aaaacttgcc aattggatta     120
aattgtgtgc aagagaccat caccatgacc accaataagg atccccaaga taaggagccc     180
gggaaagcag acaaccgac caagaatagc ggatccagcg gtgtgggtat catgaagcgc     240
ttgagaagat cggcgtccgc cacagagcat aatcttagca gtctgcgaaa ccgcaagtca     300
acacaaaatc tattcgatca gcacgggaat cccatagatc tgcgacagta tcgtaaagtt     360
ttggataagg atgaaaatgg taatggaacc aacggatccg agaagaagct tagatacagg     420
agaacacaaa gtgtgactcg tgctgaggag atttccaata agaggagaa gcagagaaga     480 gctcagcctg gcagaccaat ccatcggcca agagattctc tgttttcttg gagctctgga     540
tttaccaatt tttctggact ggtgaactgg ggatttctac tgctctgcat ggaggtctg     600 cgtttgggct tggagaatct cctaaagtat ggcattcgca tcaatccact ggattggttc     660
ttcttcataa gcggacacaa cgaaggcgaa ggacataacg ccctaatcct gagcatttac     720 tcttagtgc atatctcgct ctgtttggct gtggagaagg gtctagccat ggaaataatt     780
gcagagggct tgggcttgtt catccagata gtgaacattg ttgtcttggt ttgcctaccg     840
gtggtaacaa ttcacctaaa aggacatgct tttagtttga tgggcgcttc aacagtttgc     900 ttctttttact ctgtgttgtt cctaaaacta tggtcctatg tgcagacgaa tatgtggtgc     960
cgtcagactt attatcaaaa gaatccgcgg gagcgtcgac caagcataac tttggcggaa    1020
ctaaaaaaag gagttttgaa tggaggtgaa gaagacgagg acgtttccaa gctggtgcaa    1080
tatcctgata atctcacata caaggatctc ctgtacttcc tttgcgcgcc cactctctgc    1140
tatgagttga atttccgcg aacttctcgc gtgcgcaaac gctttttgct gaagcgttta    1200
ttggaggtgg tgattggagt gaatgtggtt atggccttgt ttcaacaatg gatcattcca    1260
```

```
tcggttcgga actccctgat tccgttctcc aatatggacg tggccttagc cactgagcga    1320
cttcttaaac ttgcgctacc caatcatctt tgctggctct gcttttttcta tctaatgttc    1380 cactctttc ttaatgcggt cggcgaactg ctgaattttg cagatcgcaa tttttattgt    1440
gattggtgga atgcgaataa cattgacacc ttctggcgta catggaacat gccagttcat    1500
aggtggtgcg tgcgtcatct ctacatccct gtggtccaaa tgggatattc ctcaagacag    1560
gcctctacta ttgtctttct tttcagtgcc gtcttccatg aatatttggt ttcagttcct    1620
ttgcaaatat acaagatctg ggcatttatg ggcatgatgg gtcagattcc cctatcggcc    1680
atatccaaat ccattgaaaa gaaactgggt ccccgaatgg gcaatataat cgtgtgggct    1740
tccattattc ttggtcagcc tctgtgcata atggcctatt atcacgatta tgtcgtccag    1800
catttcaaaa actcgctcaa cggcaccgac tacagtagtt aggtttcaaa aaaggttaac    1860
atttaaaaat ggagcaacac tgaaatatct gcatcggtcg ggtccgtgta cttttcgtaa    1920
tttataagcc agaatgcaag ttaagaagga aacttgtgat tgccaattta caaagcatat    1980
tttgtatgac ttttgcacat gcatgtagta ctgattaaca caaatagatt gttattgaat    2040
gcatttgtta atgaatttaa gtgtcatgta aataaatcaa attttaaact             2090
```

<210> SEQ ID NO 5
<211> LENGTH: 526
<212> TYPE: PRT
<213> ORGANISM: Yarrowia lipolytica

<400> SEQUENCE: 5

```
Met Glu Val Arg Arg Arg Lys Ile Asp Val Leu Lys Ala Gln Lys Asn
1               5                   10                  15

Gly Tyr Glu Ser Gly Pro Pro Ser Arg Gln Ser Ser Gln Pro Ser Ser
            20                  25                  30

Arg Ala Ser Ser Arg Thr Arg Asn Lys His Ser Ser Thr Leu Ser
        35                  40                  45

Leu Ser Gly Leu Thr Met Lys Val Gln Lys Lys Pro Ala Gly Pro Pro
    50                  55                  60

Ala Asn Ser Lys Thr Pro Phe Leu His Ile Lys Pro Val His Thr Cys
65                  70                  75                  80

Cys Ser Thr Ser Met Leu Ser Arg Asp Tyr Asp Gly Ser Asn Pro Ser
                85                  90                  95

Phe Lys Gly Phe Lys Asn Ile Gly Met Ile Ile Leu Ile Val Gly Asn
            100                 105                 110

Leu Arg Leu Ala Phe Glu Asn Tyr Leu Lys Tyr Gly Ile Ser Asn Pro
        115                 120                 125

Phe Phe Asp Pro Lys Ile Thr Pro Ser Glu Trp Gln Leu Ser Gly Leu
    130                 135                 140

Leu Ile Val Val Ala Tyr Ala His Ile Leu Met Ala Tyr Ala Ile Glu
145                 150                 155                 160

Ser Ala Ala Lys Leu Leu Phe Leu Ser Ser Lys His His Tyr Met Ala
                165                 170                 175

Val Gly Leu Leu His Thr Met Asn Thr Leu Ser Ser Ile Ser Leu Leu
            180                 185                 190

Ser Tyr Val Val Tyr Tyr Leu Pro Asn Pro Val Ala Gly Thr Ile
        195                 200                 205

Val Glu Phe Val Ala Val Ile Leu Ser Leu Lys Leu Ala Ser Tyr Ala
    210                 215                 220
```

Leu Thr Asn Ser Asp Leu Arg Lys Ala Ala Ile His Ala Gln Lys Leu
225                 230                 235                 240

Asp Lys Thr Gln Asp Asp Asn Glu Lys Glu Ser Thr Ser Ser Ser Ser
            245                 250                 255

Ser Ser Asp Asp Ala Glu Thr Leu Ala Asp Ile Asp Val Ile Pro Ala
            260                 265                 270

Tyr Tyr Ala Gln Leu Pro Tyr Pro Gln Asn Val Thr Leu Ser Asn Leu
            275                 280                 285

Leu Tyr Phe Trp Phe Ala Pro Thr Leu Val Tyr Gln Pro Val Tyr Pro
290                 295                 300

Lys Thr Glu Arg Ile Arg Pro Lys His Val Ile Arg Asn Leu Phe Glu
305                 310                 315                 320

Leu Val Ser Leu Cys Met Leu Ile Gln Phe Leu Ile Phe Gln Tyr Ala
                325                 330                 335

Tyr Pro Ile Met Gln Ser Cys Leu Ala Leu Phe Phe Gln Pro Lys Leu
            340                 345                 350

Asp Tyr Ala Asn Ile Ser Glu Arg Leu Met Lys Leu Ala Ser Val Ser
            355                 360                 365

Met Met Val Trp Leu Ile Gly Phe Tyr Ala Phe Phe Gln Asn Gly Leu
370                 375                 380

Asn Leu Ile Ala Glu Leu Thr Cys Phe Gly Asn Arg Thr Phe Tyr Gln
385                 390                 395                 400

Gln Trp Trp Asn Ser Arg Ser Ile Gly Gln Tyr Trp Thr Leu Trp Asn
                405                 410                 415

Lys Pro Val Asn Gln Tyr Phe Arg His His Val Tyr Val Pro Leu Leu
            420                 425                 430

Ala Arg Gly Met Ser Arg Phe Asn Ala Ser Val Val Phe Phe Phe
            435                 440                 445

Ser Ala Val Ile His Glu Leu Leu Val Gly Ile Pro Thr His Asn Ile
450                 455                 460

Ile Gly Ala Ala Phe Phe Gly Met Met Ser Gln Val Pro Leu Ile Met
465                 470                 475                 480

Ala Thr Glu Asn Leu Gln His Ile Asn Ser Ser Leu Gly Pro Phe Leu
            485                 490                 495

Gly Asn Cys Ala Phe Trp Phe Thr Phe Phe Leu Gly Gln Pro Thr Cys
            500                 505                 510

Ala Phe Leu Tyr Tyr Leu Ala Tyr Asn Tyr Lys Gln Asn Gln
            515                 520                 525

<210> SEQ ID NO 6
<211> LENGTH: 1581
<212> TYPE: DNA
<213> ORGANISM: Yarrowia lipolytica

<400> SEQUENCE: 6
atggaagtcc gacgacgaaa aatcgacgtg ctcaaggccc agaaaaacgg ctacgaatcg      60
ggcccaccat ctcgacaatc gtcgcagccc tcctcaagag catcgtccag aacccgcaac     120
aaacactcct cgtccaccct gtcgctcagc ggactgacca tgaaagtcca gaagaaacct     180
gcgggacccc cggcgaactc caaaacgcca ttcctacaca tcaagcccgt gcacacgtgc     240
tgctccacat caatgctttc gcgcgattat gacggctcca accccagctt caagggcttc     300
aaaaacatcg gcatgatcat tctcattgtg ggaaatctac ggctcgcatt cgaaaactac     360
ctcaaatacg gcatttccaa cccgttcttc gaccccaaaa ttactccttc cgagtggcag     420

-continued

```
ctctcaggct tgctcatagt cgtggcctac gcacatatcc tcatggccta cgctattgag    480
agcgctgcca agctgctgtt cctctctagc aaacaccact acatggccgt ggggcttctg    540
cataccatga acactttgtc gtccatctcg ttgctgtcct acgtcgtcta ctactacctg    600
cccaaccccg tggcaggcac aatagtcgag tttgtggccg ttattctgtc tctcaaactc    660
gcctcatacg ccctcactaa ctcggatctc cgaaaagccg caattcatgc ccagaagctc    720
gacaagacgc aagacgataa cgaaaaggaa tccacctcgt cttcctcttc ttcagatgac    780
gcagagactt tggcagacat tgacgtcatt cctgcatact acgcacagct gccctacccc    840
cagaatgtga cgctgtcgaa cctgctgtac ttctggtttg ctcccacact ggtctaccag    900
cccgtgtacc ccaagacgga gcgtattcga cccaagcacg tgatccgaaa cctgtttgag    960
ctcgtctctc tgtgcatgct tattcagttt ctcatcttcc agtacgccta ccccatcatg   1020
cagtcgtgtc tggctctgtt cttccagccc aagctcgatt atgccaacat ctccgagcgc   1080
ctcatgaagt tggcctccgt gtctatgatg gtctggctca ttggattcta cgctttcttc   1140
cagaacggtc tcaatcttat tgccgagctc acctgttttg aaacagaaac cttctaccag   1200
cagtggtgga attcccgctc cattggccag tactggactc tatggaacaa gccagtcaac   1260
cagtacttta gacaccacgt ctacgtgcct cttctcgctc ggggcatgtc gcggttcaat   1320
gcgtcggtgg tggttttctt tttctccgcc gtcatccatg aactgcttgt cggcatcccc   1380
actcacaaca tcatcggagc cgccttcttc ggcatgatgt cgcaggtgcc tctgatcatg   1440
gctactgaga accttcagca tattaactcc tctctgggcc ccttccttgg caactgtgca   1500
ttctggttca cctttttcct gggacaaccc acttgtgcat cctttatta tctggcttac   1560
aactacaagc agaaccagta g                                             1581
```

<210> SEQ ID NO 7
<211> LENGTH: 648
<212> TYPE: PRT
<213> ORGANISM: Yarrowia lipolytica

<400> SEQUENCE: 7

```
Met Thr Gln Pro Val Asn Arg Lys Ala Thr Val Glu Arg Val Glu Pro
1               5                   10                  15

Ala Val Glu Val Ala Asp Ser Glu Ser Glu Ala Lys Thr Asp Val His
            20                  25                  30

Val His His His His His His Lys Arg Lys Ser Val Leu Gly Lys
        35                  40                  45

Ile Leu Asn Phe Phe Thr Arg Ser Arg Arg Ile Thr Phe Val Leu Gly
    50                  55                  60

Ala Val Val Gly Val Ile Ala Ala Gly Tyr Tyr Ala Ala Pro Pro Glu
65                  70                  75                  80

Leu Ser Ile Asp Ile Asp Ala Leu Leu Gly Asp Leu Pro Ser Phe Asp
                85                  90                  95

Phe Asp Ala Leu Ser Leu Asp Asn Leu Ser Met Asp Ser Val Ser Asp
            100                 105                 110

Phe Val Gln Asp Met Lys Ser Arg Phe Pro Thr Lys Ile Leu Gln Glu
        115                 120                 125

Ala Ala Lys Ile Glu Lys His Gln Lys Ser Glu Gln Lys Ala Ala Pro
    130                 135                 140

Phe Ala Val Gly Lys Ala Met Lys Ser Glu Gly Leu Asn Ala Lys Tyr
145                 150                 155                 160

Pro Val Val Leu Val Pro Gly Val Ile Ser Thr Gly Leu Glu Ser Trp
```

```
                165                 170                 175
Ser Leu Glu Gly Thr Glu Cys Pro Thr Glu Ser His Phe Arg Lys
            180                 185                 190

Arg Met Trp Gly Ser Trp Tyr Met Ile Arg Val Met Leu Leu Asp Lys
            195                 200                 205

Tyr Cys Trp Leu Gln Asn Leu Met Leu Asp Thr Glu Thr Gly Leu Asp
            210                 215                 220

Pro Pro His Phe Lys Leu Arg Ala Ala Gln Gly Phe Ala Ser Ala Asp
225                 230                 235                 240

Phe Phe Met Ala Gly Tyr Trp Leu Trp Asn Lys Leu Leu Glu Asn Leu
            245                 250                 255

Ala Val Ile Gly Tyr Asp Thr Asp Thr Met Ser Ala Ala Tyr Asp
            260                 265                 270

Trp Arg Leu Ser Tyr Pro Asp Leu Glu His Arg Asp Gly Tyr Phe Ser
            275                 280                 285

Lys Leu Lys Ala Ser Ile Glu Glu Thr Lys Arg Met Thr Gly Glu Lys
            290                 295                 300

Thr Val Leu Thr Gly His Ser Met Gly Ser Gln Val Ile Phe Tyr Phe
305                 310                 315                 320

Met Lys Trp Ala Glu Ala Gly Tyr Gly Gly Gly Pro Asn Trp
            325                 330                 335

Val Asn Asp His Ile Glu Ser Phe Val Asp Ile Ser Gly Ser Met Leu
            340                 345                 350

Gly Thr Pro Lys Thr Leu Val Ala Leu Leu Ser Gly Glu Met Lys Asp
            355                 360                 365

Thr Val Gln Leu Asn Ala Met Ala Val Tyr Gly Leu Glu Gln Phe Phe
            370                 375                 380

Ser Arg Arg Glu Arg Ala Asp Leu Leu Arg Thr Trp Gly Gly Ile Ala
385                 390                 395                 400

Ser Met Ile Pro Lys Gly Gly Lys Ala Ile Trp Gly Asp His Ser Gly
            405                 410                 415

Ala Pro Asp Asp Glu Pro Gly Gln Asn Val Thr Phe Gly Asn Phe Ile
            420                 425                 430

Lys Phe Lys Glu Ser Leu Thr Glu Tyr Ser Ala Lys Asn Leu Thr Met
            435                 440                 445

Asp Glu Thr Val Asp Phe Leu Tyr Ser Gln Ser Pro Glu Trp Phe Val
450                 455                 460

Asn Arg Thr Glu Gly Ala Tyr Ser Phe Gly Ile Ala Lys Thr Arg Lys
465                 470                 475                 480

Gln Val Glu Gln Asn Glu Lys Arg Pro Ser Thr Trp Ser Asn Pro Leu
            485                 490                 495

Glu Ala Ala Leu Pro Asn Ala Pro Asp Leu Lys Ile Tyr Cys Phe Tyr
            500                 505                 510

Gly Val Gly Lys Asp Thr Glu Arg Ala Tyr Tyr Gln Asp Glu Pro
            515                 520                 525

Asn Pro Glu Gln Thr Asn Leu Asn Val Ser Ile Ala Gly Asn Asp Pro
            530                 535                 540

Asp Gly Val Leu Met Gly Gln Gly Asp Gly Thr Val Ser Leu Val Thr
545                 550                 555                 560

His Thr Met Cys His Arg Trp Lys Asp Glu Asn Ser Lys Phe Asn Pro
            565                 570                 575

Gly Asn Ala Gln Val Lys Val Val Glu Met Leu His Gln Pro Asp Arg
            580                 585                 590
```

Leu Asp Ile Arg Gly Gly Ala Gln Thr Ala Glu His Val Asp Ile Leu
        595                 600                 605

Gly Arg Ser Glu Leu Asn Glu Met Val Leu Lys Val Ala Ser Gly Lys
    610                 615                 620

Gly Asn Glu Ile Glu Glu Arg Val Ile Ser Asn Ile Asp Glu Trp Val
625                 630                 635                 640

Trp Lys Ile Asp Leu Gly Ser Asn
            645

<210> SEQ ID NO 8
<211> LENGTH: 1947
<212> TYPE: DNA
<213> ORGANISM: Yarrowia lipolytica

<400> SEQUENCE: 8

| | | |
|---|---|---|
| atgacacaac ctgtgaatcg gaaggcgact gtcgagcggg tcgagccagc agtggaggtg | 60 |
| gctgactccg agtccgaggc caagaccgac gtccacgttc accaccatca tcaccaccac | 120 |
| aagcgaaaat ccgtcaaggg caagattctc aacttcttca cccgaagtcg acgtatcacc | 180 |
| ttcgtcctcg cgccgtggt cggtgtgata gccgcgggat actacgctgc gccaccggag | 240 |
| ctcagcattg atatcgatgc tcttctcggc gacttgccct cgttcgactt tgacgctcta | 300 |
| tctctcgaca acttgtccat ggacagtgtg tcggactttg tacaagacat gaaatcgcgg | 360 |
| tttccgacca agattctgca ggaggcggcc aagatcgaga agcaccagaa aagcgaacag | 420 |
| aaggctgccc cttttgctgt gggcaaggct atgaagagcg agggactcaa cgccaagtac | 480 |
| ccggtggtgc tggtgcccgg cgtcatctcc acgggactgg agagctggtc cctggaggga | 540 |
| accgaggagt gtcccaccga gtcgcacttc agaaagcgaa tgtggggctc ctggtacatg | 600 |
| atccgagtca tgctgctgga caagtactgc tggctgcaga acctgatgct ggacacagag | 660 |
| accggtctag acctccccca tttcaagctg cgagccgccc agggatttgc ctccgccgac | 720 |
| ttctttatgg caggctactg gctgtggaac aagctgctcg agaacctggc tgttattgga | 780 |
| tacgatacgg atacaatgtc tgctgcggcg tacgactgga gactgtccta ccctgatttg | 840 |
| gagcaccgag acggatactt ctccaagctc aaagcttcaa tcgaagagac taagcgtatg | 900 |
| acaggtgaga gacagttct gacgggccat ccatgggct cccaggtcat cttctacttc | 960 |
| atgaagtggg ctgaggccga gggatatgga ggaggaggtc ccaactgggt caatgaccat | 1020 |
| attgaatcct tgtcgacat tccggctcc atgctgggta ctcccaagac cctggttgct | 1080 |
| cttctgtctg gagaaatgaa ggataccgtg cagctgaacg cgatggctgt gtatggactg | 1140 |
| gagcagttct tctctcgacg agagcgagcc gatctgctgc gaacatgggg aggaattgct | 1200 |
| tccatgattc ccaagggtgg taaggctatc tgggtgatc attctggagc ccctgatgac | 1260 |
| gagcctggcc agaatgtcac ctttggcaac ttcatcaagt tcaaggagtc cttgaccgag | 1320 |
| tactctgcta agaacctcac catggatgaa accgttgact tcctgtattc tcagtctccc | 1380 |
| gagtggtttg tgaaccgaac cgagggtgct tactcctttg gaattgccaa gactcgaaag | 1440 |
| caggttgagc agaatgagaa cgaccttct acctggagca accctctgga agctgctctc | 1500 |
| cccaatgccc ccgatctcaa gatctactgc ttctatggag tcggtaagga taccgagcga | 1560 |
| gcctactact accaggatga gcccaatccc gagcagacca acttgaacgt cagtatcgct | 1620 |
| ggaaacgacc ctgatggtgt gcttatgggc cagggcgatg gaaccgtctc ccttgtgacc | 1680 |
| cataccatgt gtcaccgatg gaaggacgag aattccaagt tcaaccctgg taacgcccag | 1740 |

-continued

```
gtcaaggttg tggagatgtt gcaccagcct gatcgacttg atattcgagg cggtgctcag   1800
actgccgagc atgtggacat tctggggcgt tctgagttga acgagatggt tctgaaggtg   1860
gccagtggaa agggaaatga gattgaagag agagtcatct ccaacattga tgagtgggtg   1920
tggaagattg atctcggcag caattag                                       1947
```

<210> SEQ ID NO 9
<211> LENGTH: 325
<212> TYPE: PRT
<213> ORGANISM: Fusarium oxysporum

<400> SEQUENCE: 9

```
Met Thr Thr Lys Tyr Thr Ser Val His Glu Ser Pro Asn Gly Pro Gly
1               5                   10                  15

Asp Ala Arg Pro Thr Ala Ser Gln Ile Ile Asp Asp Tyr Asn Leu Glu
            20                  25                  30

Gly Glu Leu Ser Gly Lys Thr Val Leu Val Thr Gly Cys Ser Ser Gly
        35                  40                  45

Ile Gly Val Glu Thr Ala Arg Ala Ile Tyr Arg Thr Gly Ala Thr Leu
    50                  55                  60

Tyr Leu Thr Ala Arg Asp Val Asp Lys Ala Lys Thr Val Leu Pro Asp
65                  70                  75                  80

Leu Val Asp Thr Ser Arg Val His Phe Leu His Leu Asp Leu Asn Ser
                85                  90                  95

Leu Glu Ser Val Arg Gly Phe Ala Glu Asn Phe Lys Ser Lys Ser Thr
            100                 105                 110

Gln Leu His Ile Leu Ile Glu Asn Ala Gly Val Met Ala Cys Pro Glu
        115                 120                 125

Gly Arg Thr Val Asp Gly Phe Glu Thr Gln Phe Gly Ile Asn His Leu
    130                 135                 140

Ala His Phe Leu Leu Phe Tyr Leu Leu Lys Asp Thr Leu Leu Asn Ser
145                 150                 155                 160

Ser Thr Pro Ala Phe Asn Ser Arg Val Val Ile Leu Ser Ser Cys Ala
                165                 170                 175

His Gln Ala Gly Ser Val His Leu Asn Asn Leu Ser Leu Glu Gly Gly
            180                 185                 190

Tyr Glu Pro Trp Lys Ser Tyr Gly Gln Ser Lys Thr Ala Asn Leu Trp
        195                 200                 205

Thr Ala Arg Glu Ile Glu Lys Arg Phe Gly Ala Ser Gly Ile His Ser
    210                 215                 220

Trp Ala Val His Pro Gly Ser Ile Ala Thr Glu Leu Gln Arg His Val
225                 230                 235                 240

Ser Asp Glu Leu Lys Gln Lys Trp Ala Asp Asp Lys Glu Gly Ala Lys
                245                 250                 255

Leu Trp Lys Ser Thr Glu Gln Gly Ala Ala Thr Thr Val Leu Ala Ala
            260                 265                 270

Val Ser Pro Glu Leu Glu Gly Lys Gly Leu Tyr Leu Glu Asp Thr
        275                 280                 285

Gln Val Ala Lys Pro Pro Ala Arg Gly Met Phe Gly Val Ala Asp Trp
    290                 295                 300

Ala Tyr Asp Glu Asp Gly Pro Ser Lys Leu Trp Ala Lys Ser Leu Glu
305                 310                 315                 320

Leu Leu Lys Leu Gln
                325
```

<210> SEQ ID NO 10
<211> LENGTH: 978
<212> TYPE: DNA
<213> ORGANISM: Fusarium oxysporum

<400> SEQUENCE: 10

```
atgacaacta agtacacttc ggttcacgaa agccccaacg ggcctggtga tgcgcgtccc    60
accgcttccc aaatcattga cgactataat ttagaaggag aactgtctgg caagacagtt   120
ctcgtcaccg gctgctcatc tggtattggt gttgagaccg cgcgtgcaat ctatagaaca   180
ggtgccacac tctatttgac agctcgagat gtcgacaagg ccaagacggt actgcctgat   240
ttggtagaca cttctcgcgt ccatttcctt caccttgact tgaattctct ggagtcagta   300
cgtggttttg cggaaaactt caagtcaaag agcacccaac tacatattct catcgagaac   360
gctggcgtga tggcatgccc cgagggccgt acggtggatg gatttgagac tcaatttggt   420
atcaaccacc tagctcattt cctcctcttc tatctcctca aggataccct tgctcaactct   480
tcaacgcccg ctttcaactc tcgggttgtc atcctctctt cttgtgccca tcaagcgggt   540
tcggttcact gaataaacct gagtcttgag ggagggtatg agccatggaa atcgtacggc   600
cagagcaaaa cggccaatct ctggacagca cgcgagattg agaagcgttt tggagcaagc   660
ggtatccact catgggctgt tcaccccgga agcatcgcaa cagaactgca gcgacatgtg   720
tcggacgagc ttaaacagaa gtgggcagat gataaagaag gtgccaagtt atggaaaagc   780
accgagcagg gtgcggcgac cactgtcttg gcagctgtat cgccagagct tgaaggcaaa   840
ggcgggcttt atttggagga cactcaagtt gccaagcctc cagcaagggg aatgtttggt   900
gttgcagact gggcttacga cgaagatggg ccgtctaagc tctgggccaa gagtcttgag   960
cttttgaagc tgcaatga                                                 978
```

<210> SEQ ID NO 11
<211> LENGTH: 363
<212> TYPE: PRT
<213> ORGANISM: Mucor javanicus

<400> SEQUENCE: 11

```
Met Asn Thr Ser Asn Gln Arg Tyr Ala Ser Tyr Val Val Asp Ile Lys
1               5                   10                  15
Leu Pro Pro Ala Ile Thr Val Ser Val Gly Thr Leu Thr Thr Ala Tyr
            20                  25                  30
Ala Leu Val Leu Ile Leu Asp Tyr Leu Leu Val Lys Asn Asp Ala Lys
        35                  40                  45
Phe Ser Ala Phe Val Ser Pro Met Gln Leu Arg Ala Val Ile Ala Thr
    50                  55                  60
Tyr His Phe Leu Ile Pro Ile Phe Phe Ala Ser Lys His Asp Phe Gly
65                  70                  75                  80
Asn Ile Thr Phe Met Leu His Pro Trp Ser Ile Ala Ala Gln Ile Ile
                85                  90                  95
Phe Leu Ser Ser Ser Ser Met Thr Val Lys Glu Tyr Ser Gln Thr Leu
            100                 105                 110
Leu Lys Ala Ala Val Phe Leu Asp Asp Ser Pro Thr Thr Lys Thr His
        115                 120                 125
Gln Gln Ile Arg Leu Asp Gly Met Lys Lys Val Val Arg Gly Leu Ala
    130                 135                 140
Lys Leu Ala Phe Met Lys Ile Ala Leu Asp Gly Ile Leu Pro Glu Asp
145                 150                 155                 160
```

-continued

```
Leu Ser Asp Leu Leu Ala Leu Pro Phe Tyr Ser Pro Arg Ala Met Phe
                165                 170                 175
Leu Thr Tyr Val Leu Ala Val Arg Ile Tyr Cys Met Met Ser Ile Val
            180                 185                 190
Asp Ile Pro Met Gly Val Leu Gln Ala Thr Leu Leu Ile Arg Phe His
        195                 200                 205
Asp Leu Phe Asp Asn Pro Phe Leu Ala Thr Ser Pro Lys Asp Phe Trp
    210                 215                 220
Asn Arg Arg Trp Asn Arg Met Val Lys Asn Leu Phe Gln Lys Leu Ile
225                 230                 235                 240
Phe Ser Lys Ala Ser Arg Ala Leu Asp Ala Glu Asp Lys Lys Lys
                245                 250                 255
Lys Lys Lys Thr Arg Arg Phe Val Ala Ser Pro Met Ala Phe Gly Leu
                260                 265                 270
Leu Ile Phe Phe Ile Ser Gly Leu Phe His Asp Phe Met Ile Ala Ala
            275                 280                 285
Ala Ala Arg Glu Ile Thr Phe Glu Leu Thr Val Phe Phe Leu Ile His
        290                 295                 300
Gly Phe Glu Val Ala Leu Glu Ala Lys Tyr Arg Lys Gly Lys Tyr Lys
305                 310                 315                 320
Gln Asp Pro Ser Gly Phe Thr Ala Val Val Cys Asn Leu Leu Thr Val
                325                 330                 335
Leu Phe Phe Val Thr Thr Gly Arg Leu Phe Leu Ser Pro Ile Leu Arg
            340                 345                 350
Gln Glu Val Phe Leu Lys Val Ala Gln Arg Phe
        355                 360

<210> SEQ ID NO 12
<211> LENGTH: 514
<212> TYPE: PRT
<213> ORGANISM: Fusarium fujikuroi

<400> SEQUENCE: 12

Met Asn Ser Ala Thr Val Thr Ser Ile Glu Thr Ser Asn Gly Ser Ala
1               5                   10                  15
Ser Val Ser Arg Arg Ser Gly His Asp Val Thr Gln Asn Glu Pro Asn
            20                  25                  30
Asn Ser Thr Asn Gly Asn Gly Asn Gly Thr Ala Thr Thr Lys Thr Pro
        35                  40                  45
Lys Lys Pro Gly Gln Lys Tyr Arg His Val Ala Ala Val His Lys Gln
    50                  55                  60
Thr Arg Pro Ser Cys Leu Ser His Asp Ser Asp Ala Ala Pro Ser Phe
65                  70                  75                  80
Ile Gly Phe Arg Asn Leu Met Val Ile Val Leu Val Val Gly Asn Leu
                85                  90                  95
Arg Leu Met Ile Glu Asn Ile Gln Lys Tyr Gly Val Leu Ile Cys Val
                100                 105                 110
Arg Cys His Asp Tyr Ser Arg Gln Asp Ile Tyr Leu Gly Leu Leu Leu
            115                 120                 125
Tyr Phe Leu Ile Pro Cys His Leu Leu Ala Ala Tyr Leu Ile Glu Leu
        130                 135                 140
Ala Ala Ala Gln Gln Ala Arg Gly Ser Leu Lys Arg Val Asn Asp Ser
145                 150                 155                 160
Pro Ser Gly Gly Pro Ser Glu Gln Glu Arg Lys Arg Phe His Lys Thr
```

```
                165                 170                 175
Trp Val Val Ala Trp Ala His Leu Phe Asn Ile Thr Leu Ala Leu
            180                 185                 190

Val Leu Thr Thr Trp Val Val Tyr Phe Lys Ile His His Pro Leu Ile
        195                 200                 205

Gly Thr Leu Thr Glu Met His Ala Ile Thr Val Trp Leu Lys Thr Ala
    210                 215                 220

Ser Tyr Ala Phe Thr Asn Arg Asp Leu Arg His Ala Tyr Leu His Pro
225                 230                 235                 240

Val Glu Gly Glu Arg Glu Leu Val Pro Glu Leu Tyr Thr Gln Cys Pro
                245                 250                 255

Tyr Pro Gln Asn Ile Thr Phe Ser Asn Leu Val Tyr Phe Trp Trp Ala
            260                 265                 270

Pro Thr Leu Val Tyr Gln Pro Val Tyr Pro Arg Thr Asp Lys Ile Arg
        275                 280                 285

Trp Val Phe Val Ala Lys Arg Val Gly Glu Ile Phe Gly Leu Ser Val
    290                 295                 300

Phe Met Trp Val Ala Ser Ala Gln Tyr Ala Ala Pro Val Leu Arg Asn
305                 310                 315                 320

Ser Leu Asp Lys Ile Ala Ser Leu Asp Leu Met Ser Ile Leu Glu Arg
                325                 330                 335

Leu Leu Lys Leu Ser Thr Ile Ser Leu Val Ile Trp Leu Ala Gly Phe
            340                 345                 350

Phe Ala Leu Phe Gln Ser Phe Leu Asn Ala Leu Ala Glu Val Leu Arg
        355                 360                 365

Phe Gly Asp Arg Ser Phe Tyr Asp Asp Trp Trp Asn Ser Glu Ser Leu
    370                 375                 380

Gly Ala Tyr Trp Arg Thr Trp Asn Lys Pro Val Tyr Thr Tyr Phe Lys
385                 390                 395                 400

Arg His Leu Tyr Met Pro Met Ile Gly Arg Gly Trp Ser Pro Gln Ala
                405                 410                 415

Ala Ser Phe Ala Val Phe Leu Val Ser Ala Ile Leu His Glu Ile Leu
            420                 425                 430

Val Gly Val Pro Thr His Asn Ile Ile Gly Val Ala Phe Leu Gly Met
        435                 440                 445

Phe Leu Gln Leu Pro Leu Ile Ala Leu Thr Lys Pro Leu Glu Asn Met
    450                 455                 460

Lys Leu Gly His Thr Gly Lys Ile Val Gly Asn Ser Ile Phe Trp Val
465                 470                 475                 480

Ser Phe Thr Ile Phe Gly Gln Pro Phe Ala Ala Leu Met Tyr Phe Tyr
                485                 490                 495

Ala Trp Gln Ala Lys Tyr Gly Ser Val Ser Lys Gln Met Thr Thr Val
            500                 505                 510

Ser Ser

<210> SEQ ID NO 13
<211> LENGTH: 500
<212> TYPE: PRT
<213> ORGANISM: Rattus norvegicus

<400> SEQUENCE: 13

Met Gly Asp Arg Gly Gly Ala Gly Ser Ser Arg Arg Arg Thr Gly
1               5                   10                  15

Ser Arg Val Ser Ile Gln Gly Gly Ser Gly Pro Met Val Asp Glu Glu
```

```
                20              25              30
Glu Val Arg Asp Ala Ala Val Gly Pro Asp Leu Gly Ala Gly Gly Asp
                35              40              45
Ala Pro Ala Pro Ala Pro Val Pro Ala Pro His Thr Arg Asp Lys
 50              55              60
Asp Arg Gln Thr Ser Val Gly Asp Gly His Trp Glu Leu Arg Cys His
 65              70              75              80
Arg Leu Gln Asp Ser Leu Phe Ser Ser Asp Ser Gly Phe Ser Asn Tyr
                85              90              95
Arg Gly Ile Leu Asn Trp Cys Val Val Met Leu Ile Leu Ser Asn Ala
                100             105             110
Arg Leu Phe Leu Glu Asn Leu Ile Lys Tyr Gly Ile Leu Val Asp Pro
                115             120             125
Ile Gln Val Val Ser Leu Phe Leu Lys Asp Pro Tyr Ser Trp Pro Ala
                130             135             140
Pro Cys Leu Ile Ile Ala Ser Asn Ile Phe Ile Val Ala Thr Phe Gln
145             150             155             160
Ile Glu Lys Arg Leu Ser Val Gly Ala Leu Thr Glu Gln Met Gly Leu
                165             170             175
Leu Leu His Val Val Asn Leu Ala Thr Ile Ile Cys Phe Pro Ala Ala
                180             185             190
Val Ala Leu Leu Val Glu Ser Ile Thr Pro Val Gly Ser Leu Phe Ala
                195             200             205
Leu Ala Ser Tyr Ser Ile Ile Phe Leu Lys Leu Phe Ser Tyr Arg Asp
                210             215             220
Val Asn Leu Trp Cys Arg Gln Arg Val Lys Ala Lys Ala Val Ser
225             230             235             240
Ala Gly Lys Lys Val Ser Gly Ala Ala Ala Gln Asn Thr Val Ser Tyr
                245             250             255
Pro Asp Asn Leu Thr Tyr Arg Asp Leu Tyr Tyr Phe Ile Phe Ala Pro
                260             265             270
Thr Leu Cys Tyr Glu Leu Asn Phe Pro Arg Ser Pro Arg Ile Arg Lys
                275             280             285
Arg Phe Leu Leu Arg Arg Val Leu Glu Met Leu Phe Phe Thr Gln Leu
                290             295             300
Gln Val Gly Leu Ile Gln Gln Trp Met Val Pro Thr Ile Gln Asn Ser
305             310             315             320
Met Lys Pro Phe Lys Asp Met Asp Tyr Ser Arg Ile Ile Glu Arg Leu
                325             330             335
Leu Lys Leu Ala Val Pro Asn His Leu Ile Trp Leu Ile Phe Phe Tyr
                340             345             350
Trp Leu Phe His Ser Cys Leu Asn Ala Val Ala Glu Leu Leu Gln Phe
                355             360             365
Gly Asp Arg Glu Phe Tyr Arg Asp Trp Trp Asn Ala Glu Ser Val Thr
                370             375             380
Tyr Phe Trp Gln Asn Trp Asn Ile Pro Val His Lys Trp Cys Ile Arg
385             390             395             400
His Phe Tyr Lys Pro Met Leu Arg Leu Gly Ser Asn Lys Trp Met Ala
                405             410             415
Arg Thr Gly Val Phe Leu Ala Ser Ala Phe Phe His Glu Tyr Leu Val
                420             425             430
Ser Ile Pro Leu Arg Met Phe Arg Leu Trp Ala Phe Thr Ala Met Met
                435             440             445
```

```
Ala Gln Val Pro Leu Ala Trp Ile Val Asn Arg Phe Phe Gln Gly Asn
        450                 455                 460

Tyr Gly Asn Ala Ala Val Trp Val Thr Leu Ile Ile Gly Gln Pro Val
465                 470                 475                 480

Ala Val Leu Met Tyr Val His Asp Tyr Tyr Val Leu Asn Tyr Asp Ala
                485                 490                 495

Pro Val Gly Ala
            500

<210> SEQ ID NO 14
<211> LENGTH: 488
<212> TYPE: PRT
<213> ORGANISM: Homo sapiens

<400> SEQUENCE: 14

Met Gly Asp Arg Gly Ser Ser Arg Arg Arg Thr Gly Ser Arg Pro
1               5                   10                  15

Ser Ser His Gly Gly Gly Pro Ala Ala Glu Glu Val Arg
                20                  25                  30

Asp Ala Ala Gly Pro Asp Val Gly Ala Ala Gly Asp Ala Pro Ala
                35                  40                  45

Pro Ala Pro Asn Lys Asp Gly Asp Ala Gly Val Gly Ser Gly His Trp
    50                  55                  60

Glu Leu Arg Cys His Arg Leu Gln Asp Ser Leu Phe Ser Ser Asp Ser
65                  70                  75                  80

Gly Phe Ser Asn Tyr Arg Gly Ile Leu Asn Trp Cys Val Val Met Leu
                85                  90                  95

Ile Leu Ser Asn Ala Arg Leu Phe Leu Glu Asn Leu Ile Lys Tyr Gly
                100                 105                 110

Ile Leu Val Asp Pro Ile Gln Val Val Ser Leu Phe Leu Lys Asp Pro
                115                 120                 125

Tyr Ser Trp Pro Ala Pro Cys Leu Val Ile Ala Ala Asn Val Phe Ala
    130                 135                 140

Val Ala Ala Phe Gln Val Glu Lys Arg Leu Ala Val Gly Ala Leu Thr
145                 150                 155                 160

Glu Gln Ala Gly Leu Leu Leu His Val Ala Asn Leu Ala Thr Ile Leu
                165                 170                 175

Cys Phe Pro Ala Ala Val Val Leu Leu Val Glu Ser Ile Thr Pro Val
                180                 185                 190

Gly Ser Leu Leu Ala Leu Met Ala His Thr Ile Leu Phe Leu Lys Leu
                195                 200                 205

Phe Ser Tyr Arg Asp Val Asn Ser Trp Cys Arg Arg Ala Arg Ala Lys
    210                 215                 220

Ala Ala Ser Ala Gly Lys Lys Ala Ser Ser Ala Ala Ala Pro His Thr
225                 230                 235                 240

Val Ser Tyr Pro Asp Asn Leu Thr Tyr Arg Asp Leu Tyr Tyr Phe Leu
                245                 250                 255

Phe Ala Pro Thr Leu Cys Tyr Glu Leu Asn Phe Pro Arg Ser Pro Arg
                260                 265                 270

Ile Arg Lys Arg Phe Leu Leu Arg Arg Ile Leu Glu Met Leu Phe Phe
                275                 280                 285

Thr Gln Leu Gln Val Gly Leu Ile Gln Gln Trp Met Val Pro Thr Ile
                290                 295                 300

Gln Asn Ser Met Lys Pro Phe Lys Asp Met Asp Tyr Ser Arg Ile Ile
```

```
                305                 310                 315                 320
Glu Arg Leu Leu Lys Leu Ala Val Pro Asn His Leu Ile Trp Leu Ile
                    325                 330                 335

Phe Phe Tyr Trp Leu Phe His Ser Cys Leu Asn Ala Val Ala Glu Leu
                340                 345                 350

Met Gln Phe Gly Asp Arg Glu Phe Tyr Arg Asp Trp Trp Asn Ser Glu
            355                 360                 365

Ser Val Thr Tyr Phe Trp Gln Asn Trp Asn Ile Pro Val His Lys Trp
        370                 375                 380

Cys Ile Arg His Phe Tyr Lys Pro Met Leu Arg Arg Gly Ser Ser Lys
385                 390                 395                 400

Trp Met Ala Arg Thr Gly Val Phe Leu Ala Ser Ala Phe Phe His Glu
                405                 410                 415

Tyr Leu Val Ser Val Pro Leu Arg Met Phe Arg Leu Trp Ala Phe Thr
                420                 425                 430

Gly Met Met Ala Gln Ile Pro Leu Ala Trp Phe Val Gly Arg Phe Phe
            435                 440                 445

Gln Gly Asn Tyr Gly Asn Ala Ala Val Trp Leu Ser Leu Ile Ile Gly
        450                 455                 460

Gln Pro Ile Ala Val Leu Met Tyr Val His Asp Tyr Tyr Val Leu Asn
465                 470                 475                 480

Tyr Glu Ala Pro Ala Ala Glu Ala
                485

<210> SEQ ID NO 15
<211> LENGTH: 565
<212> TYPE: PRT
<213> ORGANISM: Drosophila melanogaster

<400> SEQUENCE: 15

Met Thr Thr Asn Lys Asp Pro Gln Asp Lys Glu Pro Gly Lys Ala Glu
1               5                   10                  15

Gln Pro Thr Lys Asn Ser Gly Ser Ser Gly Val Gly Ile Met Lys Arg
                20                  25                  30

Leu Arg Arg Ser Ala Ser Ala Thr Glu His Asn Leu Ser Ser Leu Arg
            35                  40                  45

Asn Arg Lys Ser Thr Gln Asn Leu Phe Asp Gln His Gly Asn Pro Ile
        50                  55                  60

Asp Leu Arg Gln Tyr Arg Lys Val Leu Asp Lys Asp Glu Asn Gly Asn
65                  70                  75                  80

Gly Thr Asn Gly Ser Glu Lys Lys Leu Arg Tyr Arg Arg Thr Gln Ser
                85                  90                  95

Val Thr Arg Ala Glu Glu Ile Ser Asn Lys Glu Glu Lys Gln Arg Arg
                100                 105                 110

Ala Gln Pro Gly Arg Pro Ile His Arg Pro Arg Asp Ser Leu Phe Ser
            115                 120                 125

Trp Ser Ser Gly Phe Thr Asn Phe Ser Gly Leu Val Asn Trp Gly Phe
        130                 135                 140

Leu Leu Leu Cys Ile Gly Gly Leu Arg Leu Gly Leu Glu Asn Leu Leu
145                 150                 155                 160

Lys Tyr Gly Ile Arg Ile Asn Pro Leu Asp Trp Phe Phe Phe Ile Ser
                165                 170                 175

Gly His Asn Glu Gly Glu Gly His Asn Ala Leu Ile Leu Ser Ile Tyr
            180                 185                 190
```

-continued

Ser Leu Val His Ile Ser Leu Cys Leu Ala Val Glu Lys Gly Leu Ala
            195                 200                 205

Met Glu Ile Ile Ala Glu Gly Leu Gly Leu Phe Ile Gln Ile Val Asn
    210                 215                 220

Ile Val Val Leu Val Cys Leu Pro Val Val Thr Ile His Leu Lys Gly
225                 230                 235                 240

His Ala Phe Ser Leu Met Gly Ala Ser Thr Val Cys Phe Phe Tyr Ser
                245                 250                 255

Val Leu Phe Leu Lys Leu Trp Ser Tyr Val Gln Thr Asn Met Trp Cys
            260                 265                 270

Arg Gln Thr Tyr Tyr Gln Lys Asn Pro Arg Glu Arg Pro Ser Ile
        275                 280                 285

Thr Leu Ala Glu Leu Lys Lys Gly Val Leu Asn Gly Gly Glu Glu Asp
    290                 295                 300

Glu Asp Val Ser Lys Leu Val Gln Tyr Pro Asp Asn Leu Thr Tyr Lys
305                 310                 315                 320

Asp Leu Leu Tyr Phe Leu Cys Ala Pro Thr Leu Cys Tyr Glu Leu Asn
                325                 330                 335

Phe Pro Arg Thr Ser Arg Val Arg Lys Arg Phe Leu Leu Lys Arg Leu
            340                 345                 350

Leu Glu Val Val Ile Gly Val Asn Val Met Ala Leu Phe Gln Gln
    355                 360                 365

Trp Ile Ile Pro Ser Val Arg Asn Ser Leu Ile Pro Phe Ser Asn Met
    370                 375                 380

Asp Val Ala Leu Ala Thr Glu Arg Leu Leu Lys Leu Ala Leu Pro Asn
385                 390                 395                 400

His Leu Cys Trp Leu Cys Phe Phe Tyr Leu Met Phe His Ser Phe Leu
                405                 410                 415

Asn Ala Val Gly Glu Leu Leu Asn Phe Ala Asp Arg Asn Phe Tyr Cys
            420                 425                 430

Asp Trp Trp Asn Ala Asn Asn Ile Asp Thr Phe Trp Arg Thr Trp Asn
        435                 440                 445

Met Pro Val His Arg Trp Cys Val Arg His Leu Tyr Ile Pro Val Val
450                 455                 460

Gln Met Gly Tyr Ser Ser Arg Gln Ala Ser Thr Ile Val Phe Leu Phe
465                 470                 475                 480

Ser Ala Val Phe His Glu Tyr Leu Val Ser Val Pro Leu Gln Ile Tyr
                485                 490                 495

Lys Ile Trp Ala Phe Met Gly Met Met Gly Gln Ile Pro Leu Ser Ala
            500                 505                 510

Ile Ser Lys Ser Ile Glu Lys Lys Leu Gly Pro Arg Met Gly Asn Ile
        515                 520                 525

Ile Val Trp Ala Ser Ile Ile Leu Gly Gln Pro Leu Cys Ile Met Ala
    530                 535                 540

Tyr Tyr His Asp Tyr Val Val Gln His Phe Lys Asn Ser Leu Asn Gly
545                 550                 555                 560

Thr Asp Tyr Ser Ser
                565

<210> SEQ ID NO 16
<211> LENGTH: 514
<212> TYPE: PRT
<213> ORGANISM: Yarrowia lipolytica

<400> SEQUENCE: 16

```
Met Thr Ile Asp Ser Gln Tyr Tyr Lys Ser Arg Asp Lys Asn Asp Thr
1               5                   10                  15
Ala Pro Lys Ile Ala Gly Ile Arg Tyr Ala Pro Leu Ser Thr Pro Leu
            20                  25                  30
Leu Asn Arg Cys Glu Thr Phe Ser Leu Val Trp His Ile Phe Ser Ile
        35                  40                  45
Pro Thr Phe Leu Thr Ile Phe Met Leu Cys Cys Ala Ile Pro Leu Leu
    50                  55                  60
Trp Pro Phe Val Ile Ala Tyr Val Val Tyr Ala Val Lys Asp Asp Ser
65                  70                  75                  80
Pro Ser Asn Gly Gly Val Val Lys Arg Tyr Ser Pro Ile Ser Arg Asn
                85                  90                  95
Phe Phe Ile Trp Lys Leu Phe Gly Arg Tyr Phe Pro Ile Thr Leu His
                100                 105                 110
Lys Thr Val Asp Leu Glu Pro Thr His Thr Tyr Tyr Pro Leu Asp Val
            115                 120                 125
Gln Glu Tyr His Leu Ile Ala Glu Arg Tyr Trp Pro Gln Asn Lys Tyr
        130                 135                 140
Leu Arg Ala Ile Ile Ser Thr Ile Glu Tyr Phe Leu Pro Ala Phe Met
145                 150                 155                 160
Lys Arg Ser Leu Ser Ile Asn Glu Gln Glu Gln Pro Ala Glu Arg Asp
                165                 170                 175
Pro Leu Leu Ser Pro Val Ser Pro Ser Ser Pro Gly Ser Gln Pro Asp
                180                 185                 190
Lys Trp Ile Asn His Asp Ser Arg Tyr Ser Arg Gly Glu Ser Ser Gly
            195                 200                 205
Ser Asn Gly His Ala Ser Gly Ser Glu Leu Asn Gly Asn Gly Asn Asn
210                 215                 220
Gly Thr Thr Asn Arg Arg Pro Leu Ser Ser Ala Ser Ala Gly Ser Thr
225                 230                 235                 240
Ala Ser Asp Ser Thr Leu Leu Asn Gly Ser Leu Asn Ser Tyr Ala Asn
                245                 250                 255
Gln Ile Ile Gly Glu Asn Asp Pro Gln Leu Ser Pro Thr Lys Leu Lys
                260                 265                 270
Pro Thr Gly Arg Lys Tyr Ile Phe Gly Tyr His Pro His Gly Ile Ile
            275                 280                 285
Gly Met Gly Ala Phe Gly Gly Ile Ala Thr Glu Gly Ala Gly Trp Ser
    290                 295                 300
Lys Leu Phe Pro Gly Ile Pro Val Ser Leu Met Thr Leu Thr Asn Asn
305                 310                 315                 320
Phe Arg Val Pro Leu Tyr Arg Glu Tyr Leu Met Ser Leu Gly Val Ala
                325                 330                 335
Ser Val Ser Lys Lys Ser Cys Lys Ala Leu Leu Lys Arg Asn Gln Ser
            340                 345                 350
Ile Cys Ile Val Val Gly Gly Ala Gln Glu Ser Leu Leu Ala Arg Pro
        355                 360                 365
Gly Val Met Asp Leu Val Leu Leu Lys Arg Lys Gly Phe Val Arg Leu
    370                 375                 380
Gly Met Glu Val Gly Asn Val Ala Leu Val Pro Ile Met Ala Phe Gly
385                 390                 395                 400
Glu Asn Asp Leu Tyr Asp Gln Val Ser Asn Asp Lys Ser Lys Ser Leu
                405                 410                 415
```

Tyr Arg Phe Gln Gln Phe Val Lys Asn Phe Leu Gly Phe Thr Leu Pro
            420                 425                 430

Leu Met His Ala Arg Gly Val Phe Asn Tyr Asp Val Gly Leu Val Pro
        435                 440                 445

Tyr Arg Arg Pro Val Asn Ile Val Val Gly Ser Pro Ile Asp Leu Pro
450                 455                 460

Tyr Leu Pro His Pro Thr Asp Glu Glu Val Ser Glu Tyr His Asp Arg
465                 470                 475                 480

Tyr Ile Ala Glu Leu Gln Arg Ile Tyr Asn Glu His Lys Asp Glu Tyr
                485                 490                 495

Phe Ile Asp Trp Thr Glu Glu Gly Lys Gly Ala Pro Glu Phe Arg Met
            500                 505                 510

Ile Glu

<210> SEQ ID NO 17
<211> LENGTH: 543
<212> TYPE: PRT
<213> ORGANISM: Yarrowia lipolytica

<400> SEQUENCE: 17

Met Ala Thr Leu His Pro Glu Asp Ala Ala Gly Arg Pro Val Arg Arg
1               5                   10                  15

Arg Pro Arg Pro Ser Ser Gly Gly Ser Arg Ser Pro Ser Thr Lys
            20                  25                  30

Arg His Ser Ile Val Arg Glu His Leu Gly Glu Glu Leu Asn Val Pro
        35                  40                  45

Asp Gly Gln Glu Met Asp Leu Gly Gln Val Asn Lys Asn Leu Asn Ala
    50                  55                  60

Ala Tyr Ala Lys Ala Glu Lys Asp Ser Asp Glu Lys Glu Lys Lys
65                  70                  75                  80

Glu Glu Gly Val Val Asp Glu Leu Pro Glu Lys Tyr Ser Tyr Pro Arg
                85                  90                  95

Phe Ser Lys Asn Asn Arg Arg Tyr Arg Phe Thr Asp Ile Lys Phe Lys
            100                 105                 110

Pro Thr Pro Ser Ile Leu Asp Lys Phe Ala His Lys Asp Ser Glu Phe
        115                 120                 125

Phe Gly Phe Tyr Thr Leu Leu Trp Met Val Phe Ala Phe Cys Val Phe
    130                 135                 140

Arg Thr Gly Leu Leu Asn Tyr Thr Asn Glu Gly Ile Leu Phe Arg Gly
145                 150                 155                 160

Gln Ile Phe Ala Ile Leu Ser Lys Asp Leu Trp Lys Val Ala Leu Val
                165                 170                 175

Asp Leu Gly Met Tyr Leu Thr Thr Tyr Leu Ser Val Phe Leu Gln Leu
            180                 185                 190

Ala Val Lys His Gly Leu Val Asp Trp Asn Ser Phe Gly Trp Ile Ile
        195                 200                 205

Gln Asn Val His Gln Thr Leu Phe Leu Phe Phe Tyr Leu Trp Val Ala
    210                 215                 220

Lys Ser Ser Asn Leu Pro Trp Ile Gly Asn Ile Phe Ile Val Leu His
225                 230                 235                 240

Ala Phe Val Met Leu Met Lys Gln His Ser Tyr Ala Phe Tyr Asn Gly
                245                 250                 255

Tyr Leu Trp Thr Val Glu Asp Glu Leu Ser His Ala Lys Gln Arg Leu
            260                 265                 270

```
Thr Glu Asp Ile Pro Val Ser Glu Lys Glu Asp Leu Lys Leu Asp Ile
        275                 280                 285

Glu Phe Cys Glu Thr Glu Leu Lys Val Gln Ser Arg His Thr Pro Phe
        290                 295                 300

Pro Thr Asn Ile Thr Phe Ser Asn Tyr Phe Trp Tyr Ser Met Phe Pro
305                 310                 315                 320

Thr Leu Val Tyr Glu Ile Glu Phe Pro Arg Thr Pro Arg Ile Lys Trp
                325                 330                 335

Thr Tyr Val Leu Glu Lys Val Ala Ala Val Phe Gly Val Phe Phe Leu
                340                 345                 350

Met Ile Trp Val Ala Glu Ser Tyr Leu Tyr Pro Pro Val Val Ala Val
        355                 360                 365

Ile Gln Met Arg Asp Glu Pro Phe Trp Asn Lys Val Arg Ile Tyr Pro
        370                 375                 380

Ile Phe Leu Ser Asp Ile Leu Leu Pro Phe Val Ile Glu Tyr Met Leu
385                 390                 395                 400

Val Phe Tyr Ile Ile Trp Asp Ala Ile Leu Asn Gly Ile Ala Glu Leu
                405                 410                 415

Thr Arg Phe Ala Asp Arg Asp Phe Tyr Gly Pro Trp Trp Asn Cys Thr
                420                 425                 430

Ser Trp Glu Gln Phe Ser Arg Glu Trp Asn Ile Pro Val Tyr Gln Phe
        435                 440                 445

Leu Lys Arg His Val Tyr His Ser Ser Ile Ser Ala Phe Lys Phe Ser
        450                 455                 460

Lys Gly Ala Ala Thr Leu Thr Thr Phe Leu Leu Ser Ser Leu Val His
465                 470                 475                 480

Glu Leu Val Met Phe Ala Ile Phe Lys Lys Phe Arg Gly Tyr Leu Leu
                485                 490                 495

Leu Leu Gln Met Thr Gln Leu Pro Leu Ala Met Leu Gln Lys Thr Lys
                500                 505                 510

Trp Ile Gln Asp Arg Pro Val Phe Gly Asn Ala Phe Phe Trp Phe Ser
        515                 520                 525

Leu Met Ile Gly Pro Ser Leu Met Cys Ser Met Tyr Leu Leu Phe
530                 535                 540
```

PRODUCTION OF RETINYL ESTERS

This application is the U.S. national phase of International Application No. PCT/EP2018/076021 filed Sep. 25, 2018 which designated the U.S. and claims priority to U.S. Provisional Patent Application No. 62/562,680 filed Sep. 25, 2017, the entire contents of each of which are hereby incorporated by reference.

The content of the electronically submitted sequence listing (Name: 4636_3940_Sequence_Listing.txt; Size: 60.4 kilobytes; and Date of Creation: Nov. 14, 2021) is incorporated herein by reference in its entirety.

The present invention is related to a novel enzymatic process for production of retinyl esters, such as in particular retinyl long chain esters, via conversion of retinol, which process includes the use of enzymes having acyltransferase activity. Said process might be used for biotechnological production of vitamin A.

Retinyl esters, including e.g. long chain retinyl esters, are important intermediates/precursors in the process of retinoid production, particularly such as vitamin A production. Retinoids, including vitamin A, are one of very important and indispensable nutrient factors for human beings which have to be supplied via nutrition. Retinoids promote well-being of humans, inter alia in respect of vision, the immune system and growth.

Current chemical production methods for retinoids, including vitamin A and precursors thereof, have some undesirable characteristics such as e.g. high-energy consumption, complicated purification steps and/or undesirable by-products. Therefore, over the past decades, other approaches to manufacture retinoids, including vitamin A and precursors thereof, including microbial conversion steps, which would be more economical as well as ecological, have been investigated.

In general, the biological systems that produce retinoids are industrially intractable and/or produce the compounds at such low levels that commercial scale isolation is not practicable. There are several reasons for this, including instability of the retinoids in such biological systems or the relatively high production of by-products.

Thus, it is an ongoing task to improve the product-specificity and/or productivity of the enzymatic conversion of beta-carotene into vitamin A. Particularly, it is desirable to optimize the productivity of enzymes involved in conversion of retinol towards retinyl esters, such as e.g. long chain retinyl esters.

Surprisingly, we now found out that production of retinyl esters, in particular long chain retinyl esters is triggered by the use of specific enzymes having acyltransferase activity which are capable of converting retinol into long chain retinyl esters.

In particular, the present invention is directed to a host cell, particularly a carotenoid-producing host cell, particularly fungal host cell, comprising acyltransferase activity, said host cell being capable of producing, i.e. capable of enzymatically converting, retinol into retinyl long chain esters.

The terms "acyl transferase", "retinol acylating enzyme", "enzyme having retinol acylating activity" is used interchangeable herein and refers to enzymes which are capable of catalyzing the conversion of retinol into long chain retinyl esters.

The enzymes as described herein might be particularly useful in a process comprising the use of a carotenoid-producing host cell, particularly fungal host cell, capable of producing a high percentage of trans-isoforms, such as e.g. producing retinoids with a percentage of at least about 65% as trans-retinoids, including e.g. trans-retinal or trans-retinol, such as e.g. about at least 65 to 90% retinoids in trans-isoform, which might be due to action of trans-specific beta-carotene oxidase (BCO) enzymes expressed in the respective host cell. However, the acyltransferases as defined herein are capable of catalyzing either trans- or cis-retinol with the same activity.

As used herein, the term "fungal host cell" includes particularly yeast as host cell, such as e.g. *Yarrowia* or *Saccharomyces*.

The terms "conversion" or "acylation" in connection with enzymatic catalysis of retinol are used interchangeably herein and refer to the action of acyltransferases, including but not limited to DGATs, DGAs, YALs, as defined herein.

The acyltransferases as defined herein leading to production of at least about 20% long chain retinyl esters based on the total amount of retinyl esters, particularly long chain retinyl esters, are preferably introduced into a suitable host cell, such as a carotenoid-producing host cell, particularly fungal host cell, i.e. expressed as heterologous enzymes, or might be expressed as endogenous enzymes. Preferably, the enzymes as described herein are (over)expressed as heterologous enzymes.

Suitable acyltransferases according to the present invention might be obtainable from different sources, such as e.g. plants, animals, including humans, algae, fungi, including yeast, or bacteria. It comprises members of the acyl-CoA: diacylglycerol acyltransferase family [EC 2.3.1], including but not limited to DGATs [EC 2.3.1.20] such as e.g. DGAT1 or DGAT2, ARATs, mdy, in particular acyltransferases isolated from *Yarrowia*, preferably *Yarrowia lipolytica*, such as e.g. enzymes according to SEQ ID NO:5, 7 or sequences from the database (e.g., XM_504700 (SEQ ID NO: 16) *Yarrowia lipolytica* DGA2; XM_505086 (SEQ ID NO: 17) *Yarrowia lipolytica* ARE2); acyltransferases isolated from *Mucor*, preferably *Mucor circinelloides*, such as e.g. enzymes known from the database (e.g. EPB93051.1 (SEQ ID NO: 11)); acyltransferases isolated from *Fusarium*, preferably *Fusarium fujikuroi*, such as e.g. enzymes known from the database (e.g. CCT66282.1 (SEQ ID NO: 12)); acyltransferase isolated from mammals, such as e.g. human or rat, preferably *Homo sapiens* or *Rattus norvegicus*, such as e.g. enzymes known from the database (e.g. NM_053437 (SEQ ID NO: 13) or NM_012079 (SEQ ID NO: 14)); acyltransferases isolated from *Drosophila*, preferably *Drosophila melanogaster*, such as e.g. enzymes known from the database (NM_135%9 (SEQ ID NO: 3), e.g. UniProtKB sequence Q960U8 (SEQ ID NO: 15)).

In one embodiment, the polypeptides having acyltransferase activity as defined herein, i.e. increased activity towards the formation of long chain retinyl esters, via acylation of retinol, are obtainable from *Drosophila*, such as *Drosophila melanogaster*, in particular selected from polypeptides with at least about 60%, such as e.g. 65, 70, 75, 80, 85, 90, 92, 95, 97, 98, 99% or up to 100% identity to SEQ ID NO: 3, encoded by e.g. a polynucleotide sequence according to SEQ ID NO: 4, said sequences being expressed in a suitable carotenoid-producing host cell, particularly fungal host cell, and under suitable conditions as described herein. The sequences might be codon-optimized for expression in the respective host cell.

In one embodiment, the polypeptides having acyltransferase activity as defined herein, i.e. increased activity towards the formation of long chain retinyl esters, via acylation of retinol, are obtainable from *Fusarium*, such as *Fusarium fujikuroi*, in particular selected from polypeptides with at least about 60%, such as e.g. 65, 70, 75, 80, 85, 90, 92, 95, 97, 98, 99% or up to 100% identity to FfDgat1 (sequence CCT66282.1 (SEQ ID NO: 12)), said sequences being expressed in a suitable carotenoid-producing host cell, particularly fungal host cell, and under suitable conditions as described herein. The sequences might be codon-optimized for expression in the respective host cell.

In one embodiment, the polypeptides having acyltransferase activity as defined herein, i.e. increased activity towards the formation of long chain retinyl esters, via acylation of retinol, are obtainable from *Yarrowia*, such as *Yarrowia lipolytica*, in particular selected from polypeptides with at least about 60%, such as e.g. 65, 70, 75, 80, 85, 90, 92, 95, 97, 98, 99% or up to 100% identity to YlDGA2 (sequence XM_504700 (SEQ ID NO: 16)), YlARE2 (sequence XM_505086 (SEQ ID NO: 17)), SEQ ID NO:5 or 7, said sequences being expressed in a suitable carotenoid-producing host cell, particularly fungal host cell, and under suitable conditions as described herein. The sequences might be codon-optimized for expression in the respective host cell.

Preferably, the polynucleotides as described herein having acyltransferase activity are expressed on a suitable (expression)vector, which is capable of enhancing the expression of said polynucleotides cloned into it, after for instance transformation into a suitable host cell, such as a carotenoid-producing host cell, particularly fungal host cell. The cloned polynucleotides are usually operably linked to certain control sequences, such as for instance promoter sequences. The skilled person knows which (expression)vectors and/or promoters are suitable for expression in the carotenoid-producing host cells as described herein.

Modifications in order to have the host cell as defined herein produce more copies of genes and/or proteins may include the use of strong promoters, suitable transcriptional- and/or translational enhancers, or the introduction of one or more gene copies into the carotenoid-producing host cell, particularly fungal host cell, leading to increased accumulation of the respective enzymes in a given time. The skilled person knows which techniques to use in dependence of the host cell. The increase or reduction of gene expression can be measured by various methods, such as e.g. Northern, Southern, or Western blot technology as known in the art.

The generation of a mutation into nucleic acids or amino acids, i.e. mutagenesis, may be performed in different ways, such as for instance by random or side-directed mutagenesis, physical damage caused by agents such as for instance radiation, chemical treatment, or insertion of a genetic element. The skilled person knows how to introduce mutations.

Thus, the present invention is directed to a carotenoid-producing host cell, particularly fungal host cell, as described herein comprising an expression vector or a polynucleotide encoding acyltransferases as described herein which has been integrated in its chromosomal DNA. Such carotenoid-producing host cell, particularly fungal host cell, comprising a heterologous polynucleotide either on an expression vector or integrated into the chromosomal DNA encoding acyltransferases as described herein is called a recombinant host cell. The carotenoid-producing host cell, particularly fungal host cell, might contain one or more copies of a gene encoding the acyltransferases as defined herein, such as e.g. polynucleotides encoding polypeptides with at least 60% identity to known sequences according to SEQ ID NO:3, 5, 7, 9 or database sequences, e.g. XM_504700 (SEQ ID NO: 16), EPB93051.1 (SEQ ID NO: 11), XM_505086 (SEQ ID NO: 17), CCT66282.1 (SEQ ID NO: 12), NM_012079 (SEQ ID NO: 14), or NM_053437 (SEQ ID NO: 13), leading to overexpression of such genes encoding the acyltransferases as defined herein. The increase of gene expression can be measured by various methods, such as e.g. Northern, Southern, or Western blot technology as known in the art.

Based on the sequences as disclosed herein and on the preference for acylation of retinol into long chain retinyl esters, with a conversion rate of at least about 20% in the form of long chain retinyl esters, one could easily deduce further suitable genes encoding polypeptides having retinol acylating activity as defined herein which could be used for the conversion of retinol into long chain retinyl esters. Thus, the present invention is directed to a method for identification of novel retinol acylating enzymes, wherein a polypeptide with at least about 60%, such as e.g. 65, 70, 75, 80, 85, 90, 95, 97, 98, 99% or up to 100% identity to sequences SEQ ID NO:3, 5, 7, 9 or database sequences, e.g. XM_504700 (SEQ ID NO: 16), EPB93051.1 (SEQ ID NO: 11), XM_505086 (SEQ ID NO: 17), CCT66282.1 (SEQ ID NO: 12), NM_012079 (SEQ ID NO: 14), or NM_053437 (SEQ ID NO: 13) is used as a probed in a screening process for new acyltransferases with preference for production of long chain retinyl esters, either in trans- or cis-isoform. Any polypeptide having acyltransferase activity and disclosed herein might be used for production of long chain retinyl esters from retinol as described herein, as long as the acylating action results in at least about 20% long chain retinyl esters based on the total amount of produced retinoids.

The present invention is particularly directed to the use of such novel acyltransferases in a process for production of long chain retinyl esters, wherein the production of cis-isoforms might be reduced to about 20% or less based on the total amounts of retinoids. The process might be performed with a suitable carotenoid-producing host cell, particularly fungal host cell, expressing said acyltransferases, preferably wherein the genes encoding said enzymes are heterologous expressed, i.e. introduced into said host cells, furthermore expressing trans-specific enzymes, such as e.g. trans-specific BCOs catalyzing the conversion of beta-carotene to preferably trans-isoforms of retinal. Retinyl esters, in particular long chain retinyl esters, can be further converted into vitamin A by the action of (known) suitable mechanisms.

As used herein, the term "at least about 20%" with regards to production of long chain retinyl esters, means that at least about 20%, such as 30, 40, 50, 60, 70, 80, 87, 90, 92, 95, 97, 99 or up to 100% of the retinoids are long chain retinyl esters. The term "about 20% or less" with regards to production of cis-isoforms of long chain retinyl esters, means that about 20% or less, such as e.g. 18, 16, 14, 12, 10, 8, 7, 5, 2 or up to 0% of the produced long chain retinyl esters are in the form of cis-isoforms. All these numbers are based on the total amount of retinoids present in a suitable carotenoid-producing host cell, particularly fungal host cell, as defined herein.

The terms "sequence identity", "% identity" or "sequence homology" are used interchangeable herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/bases or amino acids. The sequence identity is the percentage of identical matches between the two sequences over the reported aligned region. The percent sequence identity between two amino acid sequences or between two nucleotide sequences may be determined using the Needleman and Wunsch algorithm for the alignment of two sequences (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, Longden and Bleasby, Trends in Genetics 16, (6) pp 276-277, http://emboss.bioinformatics.nl/). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: number of corresponding positions in the alignment showing an identical amino acid or identical nucleotide in both sequences divided by the total length of the alignment after subtraction of the total number of gaps in the alignment. The identity as defined herein can be obtained from NEEDLE by using the NOBRIEF option and is labeled in the output of the program as "longest identity". If both amino acid sequences which are compared do not differ in any of their amino acids, they are identical or have 100% identity. With regards to enzymes originated from plants as defined herein, the skilled person knows plant-derived enzymes might contain a chloroplast targeting signal which is to be cleaved via specific enzymes, such as e.g. chloroplast processing enzymes (CPEs).

Depending on the host cell, the polynucleotides as defined herein might be optimized for expression in the respective host cell. The skilled person knows how to generate such modified polynucleotides. It is understood that the polynucleotides as defined herein also encompass such host-optimized nucleic acid molecules as long as they still express the polypeptide with the respective activities as defined herein.

The acyltransferases as defined herein also encompasses enzymes carrying amino acid substitution(s) which do not alter enzyme activity, i.e. which show the same properties with respect to the wild-type enzyme and catalyze the conversion of retinol to long chain retinyl esters as defined herein. Such mutations are also called "silent mutations", which do not alter the (enzymatic) activity of the enzymes as described herein.

A nucleic acid molecule according to the invention may comprise only a portion or a fragment of the nucleic acid sequence provided by the present invention, such as for instance the sequences disclosed herein, such as sequences encoding XM_504700 (SEQ ID NO: 16), XM_504038 (SEQ ID NO: 7), EPB93051.1 (SEQ ID NO: 11), XM_505086 (SEQ ID NO: 17), CCT66282.1 (SEQ ID NO: 12), XM_502557 (SEQ ID NO: 5), NM_135969 (SEQ ID NO: 3), NM_012079 (SEQ ID NO: 14), NM_053437 (SEQ ID NO: 13) or according to SEQ ID NOs:1 or 2, for example a fragment which may be used as a probe or primer or a fragment encoding a portion of acyltransferases as defined herein. The nucleotide sequence determined from the cloning of the acyltransferases allows for the generation of probes and primers designed for use in identifying and/or cloning other homologues from other species. The probe/primer typically comprises substantially purified oligonucleotides which typically comprises a region of nucleotide sequence that hybridizes preferably under highly stringent conditions to at least about 12 or 15, preferably about 18 or 20, more preferably about 22 or 25, even more preferably about 30, 35, 40, 45, 50, 55, 60, 65, or 75 or more consecutive nucleotides of a nucleotide sequence as disclosed herein, such as sequences encoding XM_504700 (SEQ ID NO: 16), XM_504038 (SEQ ID NO: 7), EPB93051.1 (SEQ ID NO: 11), XM_505086 (SEQ ID NO: 17), CCT66282.1 (SEQ ID NO: 12), XM_502557 (SEQ ID NO: 5), NM_135%9 (SEQ ID NO: 3), NM_012079 (SEQ ID NO: 14), NM_053437 (SEQ ID NO: 13) or SEQ ID NO:1, 2, 4, 6, 8, 10 or a fragment or derivative thereof.

A preferred, non-limiting example of such hybridization conditions are hybridization in 6× sodium chloride/sodium citrate (SSC) at about 45° C., followed by one or more washes in 1×SSC, 0.1% SDS at 50° C., preferably at 55° C., more preferably at 60° C. and even more preferably at 65° C.

Highly stringent conditions include, for example, 2 h to 4 days incubation at 42° C. using a digoxigenin (DIG)-labeled DNA probe (prepared by using a DIG labeling system; Roche Diagnostics GmbH, 68298 Mannheim, Germany) in a solution such as DigEasyHyb solution (Roche Diagnostics GmbH) with or without 100 µg/ml salmon sperm DNA, or a solution comprising 50% formamide, 5×SSC (150 mM NaCl, 15 mM trisodium citrate), 0.02% sodium dodecyl sulfate, 0.1% N-lauroylsarcosine, and 2% blocking reagent (Roche Diagnostics GmbH), followed by washing the filters twice for 5 to 15 minutes in 2×SSC and 0.1% SDS at room temperature and then washing twice for 15-30 minutes in 0.5×SSC and 0.1% SDS or 0.1×SSC and 0.1% SDS at 65-68° C.

Expression of the enzymes/polynucleotides encoding one of the specific acyltransferases as defined herein can be achieved in any host system, including (micro)organisms, which is suitable for carotenoid/retinoid production and which allows expression of the nucleic acids encoding one of the enzymes as disclosed herein, including functional equivalents or derivatives as described herein. Examples of suitable carotenoid/retinoid-producing host (micro)organisms are bacteria, algae, fungi, including yeasts, plant, or animal cells. Preferred bacteria are those of the genera *Escherichia*, such as, for example, *Escherichia coli*, *Streptomyces*, *Pantoea* (*Erwinia*), *Bacillus*, *Flavobacterium*, *Synechococcus*, *Lactobacillus*, *Corynebacterium*, *Micrococcus*, *Mixococcus*, *Brevibacterium*, *Bradyrhizobium*, *Gordonia*, *Dietzia*, *Muricauda*, *Sphingomonas*, *Synochocystis*, *Paracoccus*, such as, for example, *Paracoccus zeaxanthinifaciens*. Preferred eukaryotic microorganisms, in particular fungi including yeast, are selected from *Saccharomyces*, such as *Saccharomyces cerevisiae*, *Aspergillus*, such as *Aspergillus niger*, *Pichia*, such as *Pichia pastoris*, *Hansenula*, such as *Hansenula polymorpha*, *Phycomyces*, such as *Phycomyces* blakesleanus, *Mucor*, *Rhodotorula*, *Sporobolomyces*, *Xanthophyllomyces*, *Phaffia*, *Blakeslea*, such as e.g. *Blakeslea trispora*, or *Yarrowia*, such as *Yarrowia lipolytica*. In particularly preferred is expression in a fungal host cell, such as e.g. *Yarrowia* or *Saccharomyces*, or expression in *Escherichia*, more preferably expression in *Yarrowia lipolytica* or *Saccharomyces cerevisiae*.

With regards to the present invention, it is understood that organisms, such as e.g. microorganisms, fungi, algae, or plants also include synonyms or basonyms of such species having the same physiological properties, as defined by the International Code of Nomenclature of Prokaryotes or the International Code of Nomenclature for algae, fungi, and plants (Melbourne Code).

As used herein, a carotenoid-producing host cell, particularly fungal host cell, is a host cell, wherein the respective polypeptides are expressed and active in vivo leading to production of carotenoids, e.g. beta-carotene. The genes and methods to generate carotenoid-producing host cells are known in the art, see e.g. WO2006102342. Depending on the carotenoid to be produced, different genes might be involved.

As used herein, a retinoid-producing host cell, particularly fungal host cell, is a host cell, wherein the respective polypeptides are expressed and active in vivo, leading to production of retinoids, e.g. vitamin A and its precursors, via enzymatic conversion of beta-carotene via retinal, retinol and retinyl esters. These polypeptides include the acyltransferases as defined herein. The genes of the vitamin A pathway and methods to generate retinoid-producing host cells are known in the art.

As used herein, a retinyl-ester mix is a mixture of retinyl esters comprising long chain retinyl esters. It might furthermore include other ester forms, such as retinyl acetate. Preferably, such a mix is high in trans-isoforms, such as e.g. comprising at least about 20% retinyl esters, particularly long chain trans retinyl esters, in the trans-isoform. The term "long chain retinyl ester" defines hydrocarbon esters that consists of at least about 8, such as e.g. 9, 10, 12, 13, 15 or 20 carbon atoms and up to about 26, such as e.g. 25, 22, 21 or less carbon atoms, with preferably up to about 6 unsaturated bonds, such as e.g. 0, 1, 2, 4, 5, 6 unsaturated bonds. Long chain retinyl esters include but are not limited to linoleic acid, oleic acid, or palmitic acid.

The present invention is directed to a process for production of long chain retinyl esters, i.e. retinoids with a percentage of at least 20% of long chain retinyl esters, either in the trans- or cis-isoform, preferably in trans-isoform, via acylation of retinol by the action of acyltransferases as described herein, wherein the acylating enzymes are preferably heterologous expressed in a suitable host cell under suitable conditions as described herein. The produced long chain retinyl esters, might be isolated and optionally further purified from the medium and/or host cell. In a further embodiment, long chain retinyl esters, can be used as precursor in a multi-step process leading to vitamin A. Vitamin A might be isolated and optionally further purified from the medium and/or host cell as known in the art.

The host cell, i.e. microorganism, algae, fungal, animal or plant cell, which is able to express the beta-carotene producing genes, the acyltransferases as defined herein, optionally the genes encoding beta-carotene oxygenating enzymes, optionally the genes encoding retinal reducing enzymes and/or optionally further genes required for biosynthesis of vitamin A, may be cultured in an aqueous medium supplemented with appropriate nutrients under aerobic or anaerobic conditions and as known by the skilled person for the different host cells. Optionally, such cultivation is in the presence of proteins and/or co-factors involved in transfer of electrons, as defined herein. The cultivation/growth of the host cell may be conducted in batch, fed-batch, semi-continuous or continuous mode. Depending on the host cell, preferably, production of retinoids such as e.g. vitamin A and precursors such as retinal, retinal, retinyl esters can vary, as it is known to the skilled person. Cultivation and isolation of beta-carotene and retinoid-producing host cells selected from *Yarrowia* is described in e.g. WO2008042338. With regards to production of retinoids in host cells selected from *E. coli*, methods are described in e.g. Jang et al, Microbial Cell Factories, 10:95 (2011). Specific methods for production of beta-carotene and retinoids in yeast host cells, such as e.g. *Saccharomyces cerevisiae*, are disclosed in e.g. WO2014096992.

As used herein, the term "specific activity" or "activity" with regards to enzymes means its catalytic activity, i.e. its ability to catalyze formation of a product from a given substrate. The specific activity defines the amount of substrate consumed and/or product produced in a given time period and per defined amount of protein at a defined temperature. Typically, specific activity is expressed in µmol substrate consumed or product formed per min per mg of protein. Typically, µmol/min is abbreviated by U (=unit). Therefore, the unit definitions for specific activity of µmol/min/(mg of protein) or U/(mg of protein) are used interchangeably throughout this document. An enzyme is active, if it performs its catalytic activity in vivo, i.e. within the host cell as defined herein or within a system in the presence of a suitable substrate. The skilled person knows how to measure enzyme activity, in particular activity of acyltransferases as defined herein. Analytical methods to evaluate the capability of a suitable acyltransferase as defined herein for retinyl ester production, particularly long chain retinyl ester production, from conversion of retinal are known in the art, such as e.g. described in Example 4 of WO2014096992. In brief, titers of products such as retinyl esters, particularly long chain retinyl esters, retinal, trans-retinal, cis-retinal, beta-carotene and the like can be measured by HPLC.

Retinoids as used herein include beta carotene cleavage products also known as apocarotenoids, including but not limited to retinal, retinolic acid, retinal, retinoic methoxide, retinyl acetate, retinyl esters, 4-keto-retinoids, 3 hydroxy-retinoids or combinations thereof. A mixture comprising retinal, retinol and retinyl esters is referred to herein as "retinoid mix". Biosynthesis of retinoids is described in e.g. WO2008042338.

Retinal as used herein is known under IUPAC name (2E,4E,6E,8E)-3,7-Dimethyl-9-(2,6,6-trimethylcyclohexen-1-yl)nona-2,4,6,8-tetraenal. It is herein interchangeably referred to as retinaldehyde or vitamin A aldehyde and includes both cis- and trans-isoforms, such as e.g. 11-cis retinal, 13-cis retinal, trans-retinal and all-trans retinal.

The term "carotenoids" as used herein is well known in the art. It includes long, 40 carbon conjugated isoprenoid polyenes that are formed in nature by the ligation of two 20 carbon geranylgeranyl pyrophosphate molecules. These include but are not limited to phytoene, lycopene, and carotene, such as e.g. beta-carotene, which can be oxidized on the 4-keto position or 3-hydroxy position to yield canthaxanthin, zeaxanthin, or astaxanthin. Biosynthesis of carotenoids is described in e.g. WO2006102342.

Vitamin A as used herein may be any chemical form of vitamin A found in aqueous solutions, such as for instance undissociated, in its free acid form or dissociated as an anion. The term as used herein includes all precursors or intermediates in the biotechnological vitamin A pathway. It also includes vitamin A acetate.

In particular, the present invention features the present embodiments:

A carotenoid-producing host cell, particularly fungal host cell, comprising an enzyme with retinol acylating activity, preferably acyltransferase [EC 2.3.1] activity, more preferably acyltransferase [EC 2.3.1.20] activity, said host cell producing long chain retinyl esters with a percentage of at least about 20% based on the total amount of retinoids produced by said host cell.

A carotenoid-producing host cell, particularly fungal host cell, as above and defined herein, comprising an enzyme with retinol acylating activity, preferably acyltransferase [EC 2.3.1] activity, more preferably acyltransferase [EC 2.3.1.20] activity, said host cell producing a retinyl ester mix comprising long chain retinyl esters, wherein the mix comprises at least about 20% such as 30, 40, 50, 60, 70, 80, 87, 90, 92, 95, 97, 99 or up to 100% long chain retinyl esters in trans-isoform.

The carotenoid-producing host cell, particularly fungal host cell, as above and defined herein, wherein the retinyl ester is selected from long chain retinyl esters.

The carotenoid-producing host cell, particularly fungal host cell, as above and defined herein comprising a heterologous acyltransferase.

The carotenoid-producing host cell, particularly fungal host cell, as above and as defined herein, wherein the host cell is selected from plants, fungi, algae or microorganisms, preferably selected from the group consisting of *Escherichia, Streptomyces, Pantoea, Bacillus, Ravobacterium, Synechococcus, Lactobacillus, Corynebacterium, Micrococcus, Mixococcus, Brevibacterium, Bradyrhizobium, Gordonia, Dietzia, Muricauda, Sphingomonas, Synochocystis, Paracoccus, Saccharomyces, Aspergillus, Pichia, Hansenula, Phycomyces, Mucor, Rhodotorula, Sporobolomyces, Xanthophyllomyces, Phaffia, Blakeslea* and *Yarrowia*, more preferably from *Yarrowia lipolytica* or *Saccharomyces cerevisiae*.

The carotenoid-producing host cell, particularly fungal host cell, as above and defined herein, wherein the acyltransferase is selected from plants, animals, including humans, algae, fungi, including yeast, or bacteria, preferably selected from the group consisting of *Drosophila, Fusarium, Mucor*, human, rat and *Yarrowia*.

The carotenoid-producing host cell, particularly fungal host cell, as above and defined herein, wherein the acyltransferase is acyltransferase selected from *Yarrowia* or *Drosophila*, preferably selected from *Y. lipolytica* or *D. melanogaster*.

The carotenoid-producing host cell, particularly fungal host cell, as above and defined herein, wherein the acyltransferase is selected from a polypeptide with at least about 60% identity to acyltransferase according to sequence XM_502557 (SEQ ID NO: 5), sequence NM_135969 (SEQ ID NO: 3) or encoded by a polynucleotide according to SEQ ID NOs:1 and 2.

The carotenoid-producing host cell, particularly fungal host cell, as above and defined herein, wherein the retinyl ester comprising long chain retinyl esters is further converted into vitamin A.

A process for production of a retinyl ester mix comprising long chain retinyl esters via enzymatic activity of acyltransferase [EC 2.3.1], comprising contacting retinol with said acyltransferase, wherein the ratio of trans- to cis-isoforms in the mix is at least about 4.

A process for decreasing the amount of cis-isoforms in a retinoid mix produced from enzymatic action of acyltransferase, said process comprising contacting retinol with acyltransferase, wherein the amount of cis-retinyl esters in the retinoid mix resulting from said enzymatic action is reduced by at least 20% compared to the amount in the retinoid mix prior to the contact with the enzyme.

A process for increasing the amount of trans-isoforms in a retinoid mix produced from enzymatic action of acyltransferase, said process comprising contacting retinol with an acyltransferase, wherein the amount of trans-retinyl esters in the retinoid mix resulting from said enzymatic action is increased by at least about 20% compared to the amount in the retinoid mix prior to the contact with the enzyme.

A process according as above and defined herein using the carotenoid-producing host cell, particularly fungal host cell, comprising an enzyme with retinol acylating activity, preferably acyltransferase [EC 2.3.1] activity, more preferably acyltransferase [EC 2.3.1.20] activity, said host cell producing a retinyl ester mix comprising long chain retinyl esters, wherein the mix comprises at least about 20%, such as 30, 40, 50, 60, 70, 80, 87, 90, 92, 95, 97, 99 or up to 100% retinyl esters in trans-isoform.

A process for production of vitamin A comprising the steps of:
(a) introducing a nucleic acid molecule encoding acyltransferase [EC 2.3.1] as defined herein into a suitable carotene-producing host cell, particularly fungal host cell,
(b) enzymatic conversion of retinol into a long chain retinyl ester mix comprising trans- and cis-retinyl esters in a ratio of at least about 4,
(c) conversion of retinyl esters into vitamin A under suitable culture conditions.

Use of acyltransferase [EC 2.3.1] as defined for production of a long chain retinyl ester mix comprising trans- and cis-retinyl esters in a ratio of at least about 4, wherein the acyltransferase is heterologous expressed in a suitable carotenoid-producing host cell, particularly fungal host cell.

The following examples are illustrative only and are not intended to limit the scope of the invention in any way. The contents of all references, patent applications, patents, and published patent applications, cited throughout this application are hereby incorporated by reference, in particular WO2006102342, WO2008042338 or WO2014096992.

EXAMPLES

Example 1: General Methods, Strains, and Plasmids

All basic molecular biology and DNA manipulation procedures described herein are generally performed according to Sambrook et al. (eds.), Molecular Cloning: A Laboratory Manual. Cold Spring Harbor Laboratory Press: New York (1989) or Ausubel et al. (eds). Current Protocols in Molecular Biology. Wiley: New York (1998).

Shake plate assay. Typically, 800 µl of 0.075% Yeast extract, 0.25% peptone (0.25×YP) is inoculated with 10p of freshly grown *Yarrowia* and overlaid with 200 µl of Drakeol 5 mineral oil carbon source 5% corn oil in mineral oil and/or 5% in glucose in aqueous phase. Transformants were grown in 24 well plates (Multitron, 30° C., 800 RPM) in YPD media with 20% dodecane for 4 days. The mineral oil fraction was removed from the shake plate wells and analyzed by HPLC on a normal phase column, with a photodiode array detector.

DNA transformation. Strains are transformed by overnight growth on YPD plate media 50 µl of cells is scraped from a plate and transformed by incubation in 500 µl with 1 µg transforming DNA, typically linear DNA for integrative transformation, 40% PEG 3550MW, 100 mM lithium acetate, 50 mM Dithiothreitol, 5 mM Tris-CL pH 8.0, 0.5 mM EDTA for 60 minutes at 40° C. and plated directly to selective media or in the case of dominant antibiotic marker selection the cells are out grown on YPD liquid media for 4 hours at 30° C. before plating on the selective media.

DNA molecular biology. Genes were synthesized with NheI and MluI ends in pUC57 vector. Typically, the genes were subcloned to the MB5082 'URA3', MB6157 HygR, and MB8327 NatR vectors for marker selection in *Yarrowia lipolytica* transformations, as in WO2016172282. For clean gene insertion by random nonhomologous end joining of the gene and marker HindIII/XbaI (MB5082) or PvuII (MB6157 and MB8327), respectively purified by gel electrophoresis and Qiagen gel purification column.

Plasmid list. Plasmid, strains, and codon-optimized sequences to be used are listed in Table 1, 2 and the sequence listing. All sequences were the same as the accession sequence in the database as nucleotides (nt), except for the numbered sequence ID NOs: 1, 2 that were codon optimized for expression in *Yarrowia*.

TABLE 1 list of plasmids used for construction of the strains carrying the heterologous acyltransferase-genes of *Yarrowia lipolytica* (YlDGA1), sequence XM_502557 and *Drosophila melanogaster* (Dm Dgat1), sequence NM_135969. For more details, see text.

| MB plasmid | Backbone MB | Insert | SEQ ID NO: (codon-optimized) |
|---|---|---|---|
| 8201 | 5082 | DmDGA1 | 1 |
| 8299 | 5082 | YlDGA1 | 2 |

TABLE 2 list of *Yarrowia* strains used for production of retinoids carrying the heterologous acyltransferase genes. For more details, see text.

| ML strain | Description | First described in |
|---|---|---|
| 7788 | Carotene strain | WO2016172282 |
| 15710 | ML7788 transformed with MB7311 -Mucor CarG | WO2016172282 |
| 17544 | ML15710 cured of URA3 by FOA and HygR by Cre/lox | here |
| 17767 | ML17544 transformed with MB6072 DmBCO-URA3 and MB6732 SbATF1-HygR and cured of markers | here |
| 17978 | ML17968 transformed with MB8200 FfRDH-URA3 and cured of markers | here |

Normal phase retinol method. A Waters™ 1525 binary pump attached to a Waters™ 717 auto sampler were used to inject samples. A Phenomenex Luna 3µ Silica (2), 150×4.6 mm with a security silica guard column kit was used to resolve retinoids. The mobile phase consists of either, 1000 mL hexane, 30 mL isopropanol, and 0.1 mL acetic acid for astaxanthin related compounds, or 1000 mL hexane, 60 mL isopropanol, and 0.1 mL acetic acid for zeaxanthin related compounds. The flow rate for each is 0.6 mL per minute. Column temperature is ambient. The injection volume is 20 µL. The detector is a photodiode array detector collecting from 210 to 600 nm. Analytes were detected according to Table 3.

TABLE 3 list of analytes using normal phase retinol method. For more details, see text.

| Intermediates | Retention time [min] | Lambda max [nm] |
|---|---|---|
| 11-cis-dihydro-retinol | 7.1 | 293 |
| 11-cis-retinal | 4 | 364 |
| 11-cis-retinol | 8.6 | 318 |
| 13-cis-retinal | 4.1 | 364 |
| dihydro-retinol | 9.2 | 292 |
| retinyl-acetate | 3.5 | 326 |
| retinyl-ester | 3 | 325 |
| trans-retinal | 4.7 | 376 |
| trans-retinol | 10.5 | 325 |

Sample preparation. Samples were prepared by various methods depending on the conditions. For whole broth or washed broth samples the broth was placed in a Precellys® tube weighed and mobile phase was added, the samples were processed in a Precellys® homogenizer (Bertin Corp, Rockville, MD, USA) on the highest setting 3× according to the manufactures directions. In the washed broth the samples were spun in a 1.7 ml tube in a microfuge at 10000 rpm for 1 minute, the broth decanted, 1 ml water added mixed pelleted and decanted and brought up to the original volume the mixture was pelleted again and brought up in appropriate amount of mobile phase and processed by Precellys® bead beating. For analysis of mineral oil fraction, the sample was spun at 4000 RPM for 10 minutes and the oil was decanted off the top by positive displacement pipet (Eppendorf, Hauppauge, NY, USA) and diluted into mobile phase mixed by vortexing and measured for retinoid concentration by HPLC analysis.

Fermentation conditions. Fermentations were identical to the previously described conditions using mineral oil overlay and stirred tank that was corn oil fed in a bench top reactor with 0.5 L to 5 L total volume (see WO2016172282). Generally, the same results were observed with a fed batch stirred tank reactor with an increased productivity demonstrating the utility of the system for the production of retinoids.

Example 2: Production of Retinoids in *Yarrowia lipolytica*

Retinol producing strain ML17767 was transformed with purified HinDIII/XbaI gene fragments containing codon optimized acyltransferase genes linked to URA3 nutritional marker and selected on minimal media without uracil. Multiple isolates were screened in a shake plate assay for increased acylation of retinol and decreased residual retinol. Successful isolates were run in fed batch stirred tank reactors to show utility of the method for increased production of retinol esters. The result of the experiment is shown below indicating that we have isolated genes with increased retinol acylation activity in a fungal production system.

TABLE 4

Retinoid production in *Yarrowia* as enhanced by action of heterologous acyltransferase enzymes. "% ester" means percentage of long chain retinyl esters in the mix of retinoids. For more details, see text.

| Organism | Accession no. | % increased ester- | ML strain | MB plasmid | SEQ ID NO: (aa/nt) |
|---|---|---|---|---|---|
| D. melanogaster | NM_135969 | 14% | 17767 | 8299 | 3/4 |
| Y. lipolytica | XM_502557 | 20% | 17767 | 8201 | 5/6 |
| Y. lipolytica | XM_504038 | 0 | 17767 | 8195 | 7/8 |
| F. oxysporum | EXK27040 | 10% | 17767 | 8200 | 9/10 |

Example 3: Production of Retinoids in *Saccharomyces cerevisiae*

Typically, a beta carotene strain is transformed with heterologous genes encoding for enzymes such as geranylgeranyl synthase, phytoene synthase, lycopene synthase, lycopene cyclase constructed that is producing beta carotene according to standard methods as known in the art (such as e.g. as described in US20160130628 or WO2009126890). By introducing and/or overexpressing the acyltransferase enzymes as defined herein, similar results regarding production of long chain retinyl esters, are obtained. Further, when transformed with beta carotene oxidase genes retinal can be produced. Further, when transformed with retinol dehydrogenase, then retinol can be produced. With this approach, similar results regarding productivity towards long chain retinyl esters are obtained.

The invention claimed is:

1. A process for production of retinoids comprising a long chain retinyl ester mix, wherein the process comprises contacting retinol with an acyltransferase [EC 2.3.1] comprising an amino acid sequence having at least 90% identity to SEQ ID NO: 3 or 5, wherein the ratio of trans- to cis-isoforms in the long chain retinyl ester mix is at least 4.

2. A process of culturing a carotenoid-producing host cell comprising contacting the host cell with a medium under suitable culture conditions, wherein the host cell comprises a heterologous acyltransferase [EC 2.3.1.20] enzyme with retinol acylating activity, wherein the heterologous acyltransferase comprises an amino acid sequence having at least 90% identity to SEQ ID NO: 3 or 5, and wherein said host cell is capable of producing long chain retinyl esters with a percentage of at least 20% based on the total amount of retinoids produced by said host cell.

3. A process for production of vitamin A comprising the steps of:
(a) introducing a nucleic acid molecule encoding an acyltransferase [EC 2.3.1] comprising an amino acid sequence having at least 90% identity to SEQ ID NO: 3 or 5 into a suitable carotene-producing host cell, and
(b) culturing the host cell under suitable conditions, whereby retinol is enzymatically converted into a long chain retinyl ester mix comprising trans- and cis-retinyl esters in a ratio of at least 4, and the long chain retinyl esters are converted into vitamin A.

4. A process for production of a long chain retinyl ester mix comprising trans- and cis-retinyl esters in a ratio of at least 4,
which process comprises culturing a host cell under suitable conditions, wherein the host cell is a carotenoid-producing host cell that expresses a heterologous EC 2.3.1 acyltransferase with retinol acylating activity, wherein the heterologous acyltransferase comprises an amino acid sequence having at least 90% identity to SEQ ID NO: 3 or 5.

5. The process of claim 4, wherein the host cell produced long chain retinyl esters with a percentage of at least 20% based on the total amount of retinoids produced by the host cell.

6. The process of claim 4, wherein the host cell is selected from plants, fungi, algae and microorganisms.

7. The process of claim 4, wherein the host cell is selected from the group consisting of *Escherichia, Streptomyces,*

*Pantoea, Bacillus, Flavobacterium, Synechococcus, Lactobacillus, Corynebacterium, Micrococcus, Mixococcus, Brevibacterium, Bradyrhizobium, Gordonia, Dietzia, Muricauda, Sphingomonas, Synochocystis, Paracoccus, Saccharomyces, Aspergillus, Pichia, Hansenula, Phycomyces, Mucor, Rhodotorula, Sporobolomyces, Xanthophyllomyces, Phaffia, Blakeslea* and *Yarrowia*.

8. The process of claim 4, wherein the host cell is *Yarrowia lipolytica* or *Saccharomyces cerevisiae*.

9. The process of claim 4, wherein the long chain retinyl esters are further converted into vitamin A.

10. The process of claim 1, wherein the acyltransferase comprises an amino acid sequence having at least 90% identity to SEQ ID NO: 3.

11. The process of claim 2, wherein the heterologous acyltransferase comprises an amino acid sequence having at least 90% identity to SEQ ID NO: 3.

12. The process of claim 3, wherein the acyltransferase comprises an amino acid sequence having at least 90% identity to SEQ ID NO: 3.

13. The process of claim 4, wherein the heterologous acyltransferase comprises an amino acid sequence having at least 90% identity to SEQ ID NO: 3.

\* \* \* \* \*